United States Patent
Anderson

(10) Patent No.: US 9,274,124 B2
(45) Date of Patent: Mar. 1, 2016

(54) MASS SPECTROMETRIC ASSAYS FOR PEPTIDES

(75) Inventor: Norman Leigh Anderson, Washington, DC (US)

(73) Assignee: ANDERSON FORSCHUNG GROUP, INC., Washington, DC (US)

( * ) Notice: Subject to any disclaimer, the term of this patent is extended or adjusted under 35 U.S.C. 154(b) by 0 days.

(21) Appl. No.: 13/635,668

(22) PCT Filed: Mar. 15, 2011

(86) PCT No.: PCT/US2011/028569
§ 371 (c)(1),
(2), (4) Date: Oct. 4, 2012

(87) PCT Pub. No.: WO2011/116028
PCT Pub. Date: Dec. 22, 2011

(65) Prior Publication Data
US 2013/0040857 A1    Feb. 14, 2013

Related U.S. Application Data

(60) Provisional application No. 61/314,149, filed on Mar. 15, 2010, provisional application No. 61/314,154, filed on Mar. 15, 2010.

(51) Int. Cl.
| | |
|---|---|
| C40B 30/10 | (2006.01) |
| G01N 33/68 | (2006.01) |
| G01N 30/72 | (2006.01) |
| G01N 30/04 | (2006.01) |
| G01N 30/88 | (2006.01) |

(52) U.S. Cl.
CPC ........ *G01N 33/6848* (2013.01); *G01N 30/7233* (2013.01); *G01N 2030/045* (2013.01); *G01N 2030/8831* (2013.01); *G01N 2458/15* (2013.01)

(58) Field of Classification Search
CPC ................. G01N 33/6848; G01N 2458/15
See application file for complete search history.

(56) References Cited

U.S. PATENT DOCUMENTS

| | | | |
|---|---|---|---|
| 7,052,916 B2 * | 5/2006 | Johnson | 436/86 |
| 2003/0219838 A1 * | 11/2003 | Johnson | 435/7.5 |
| 2005/0037482 A1 | 2/2005 | Braig et al. | |
| 2005/0208550 A1 | 9/2005 | Pappin et al. | |
| 2005/0255464 A1 | 11/2005 | Hagen et al. | |
| 2006/0154318 A1 | 7/2006 | Anderson | |
| 2006/0155186 A1 | 7/2006 | James | |
| 2006/0188911 A1 | 8/2006 | Otomo et al. | |
| 2008/0118462 A1 | 5/2008 | Alani et al. | |

OTHER PUBLICATIONS

Anderson, N. Leigh et al 2004 Journal of Proteome Research 3: 235-244.*
Zhang et al. Identification and quantification of N-linked glycoproteins using hydrazide chemistry, stable isotope labeling and mass spectrometry. Nature Biotechnology, 2003, vol. 21, No. 6, pp. 660-666.*
Aubry et al. MALDI TOF mass spectrometry: A powerful tool to study the internalization of cell-penetrating peptides. Biochimica et Biophysica Acta, 2010 vol. 1798, pp. 2182-2189.*
Whiteaker et al. Antibody-based enrichment of peptides on magnetic beads for mass-spectrometry-based quantification of serum biomarkers. Analytical Biochemistry, 2007, vol. 362, pp. 44-54.*
Anderson et al. Mass spectrometric quantitation of peptides and proteins using Stable Isotope Standards and Capture by Anti-Peptide Antibodies (SISCAPA). J Proteome Res. Mar.-Apr. 2004, vol. 3, No. 2, pp. 235-244.*
Anderson et al. SISCAPA Peptide Enrichment on Magnetic Beads Using and In-Line Bead Trap Device. Mol Cell Proteomics. May 2009; 8(5): 995-1005.*
Xu et al. Immunoaffinity Purification Using Anti-PEG Antibody Followed by Two-Dimensional Liquid Chromatography/Tandem Mass Spectrometry for the Quantification of a PEGylated Therapeutic Peptide in Human Plasma. Anal Chem 2010, 82, 6877-6886.*

* cited by examiner

*Primary Examiner* — Marcela M Cordero Garcia
(74) *Attorney, Agent, or Firm* — Perkins Coie LLP

(57) ABSTRACT

Methods for interpretation of mass spectrometric tests for clinical biomarkers in which the amounts of internal standards are set to equal clinical evaluation thresholds, and preparations for adding stable isotope labeled peptide species to sample digests while minimizing losses and alterations in peptide stoichiometry.

24 Claims, 6 Drawing Sheets

A

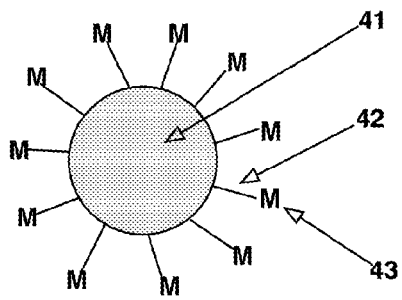

MSGSHHHHHHSSGIEGRGRLIKHMTMAKATEHLS
TLSEKNWGLSVYADKPETTKILGGHLDAKDTVQI
HDITGKTVIGPDGHKQGFGNVATNTDGKEIGELY
LPKTGLQEVEVKDDLYVSDAFHKIYHSHIDAPKE
TAASLLQAGYKITQVLHFTKFPEVDVLTKLGNQE
PGGQTALKLSSPAVITDKQWAGLVEKIPPWEAPK
LFLEPTQADIALLKSHAPEVITSSPLKIFYNQQN
HYDGSTGKEHSSLAFWKVSVSQTSKESDTSYVSL
KWELDLDIKSTVLTIPEIIIKLIENGYFHPVKAS
YPDITGEKDPPSDLLLLKALQDQLVLVAAKAEIEYLEKQPGGIRGSGC

B

MSGSHHHHHHSSGIEGRGRLIKHMTMAKATEHLS
TLSEKNWGLSVYADKPETTKILGGHLDAKDTVQI
HDITGKTVIGPDGHKQGFGNVATNTDGKEIGELY
LPKTGLQEVEVKDDLYVSDAFHKIYHSHIDAPKE
TAASLLQAGYKITQVLHFTKFPEVDVLTKLGNQE
PGGQTALKLSSPAVITDKQWAGLVEKIPPWEAPK
LFLEPTQADIALLKSHAPEVITSSPLKIFYNQQN
HYDGSTGKEHSSLAFWKVSVSQTSKESDTSYVSL
KWELDLDIKSTVLTIPEIIIKLIENGYFHPVKAS
YPDITGEKDPPSDLLLLKALQDQLVLVAAKAEIEYLEKQPGGIRGSGCM

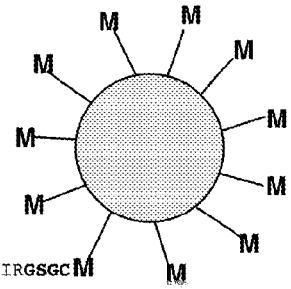

C

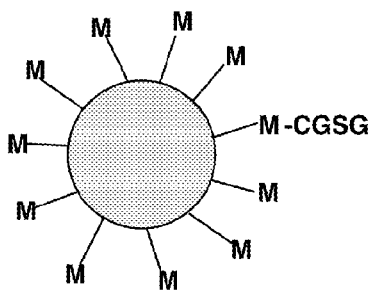

MSGSHHHHHHSSGIE      LSSPAVITDK
GR                   QWAGLVEK
GRLIK                IPPWEAPK
HMTMAK               LFLEPTQADIALLK
ATEHLSTLSEK          SHAPEVITSSPLK
NWGLSVYADKPETTK      IFYNQQNHYDGSTGK
ILGGHLDAK            EHSSLAFWK
DTVQIHDITGK          VSVSQTSK
TVIGPDGHK            ESDTSYVSLK
QGFGNVATNTDGK        WELDLDIK
EIGELYLPK            STVLTIPEIIIK
TGLQEVEVK            LIENGYFHPVK
DDLYVSDAFHK          ASYPDITGEK
IYHSHIDAPK           DPPSDLLLLK
ETAASLLQAGYK         ALQDQLVLVAAK
ITQVLHFTK            AEIEYLEK
FPEVDVLTK            QPGGIR
LGNQEPGGQTALK

Figure 7

SEQUENCE LISTING

```
<160> NUMBER OF SEQ ID NOS: 45

<210> SEQ ID NO 1
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 1

Gly Ser Gly Lys
1

<210> SEQ ID NO 2
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 2

Gly Ser Gly Ser Gly
1               5

<210> SEQ ID NO 3
<211> LENGTH: 4
<212> TYPE: PRT
```

```
<213> ORGANISM: Artificial Sequence
<220> FEATURE:
<223> OTHER INFORMATION: Synthetic Peptide

<400> SEQUENCE: 3

Cys Gly Ser Gly
1

<210> SEQ ID NO 4
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 4

Phe Ser Pro Asp Asp Ser Ala Gly Ala Ser Ala Leu Leu Arg
1               5                   10

<210> SEQ ID NO 5
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 5

Glu Ile Gly Glu Leu Tyr Leu Pro Lys
1               5

<210> SEQ ID NO 6
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 6

Cys Gly Ser Gly Lys Glu Ile Gly Glu Leu Tyr Leu Pro Lys
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 7

Cys Gly Ser Gly Lys Glu Ile Gly Glu Leu Tyr Leu Pro Lys
1               5                   10

<210> SEQ ID NO 8
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 8

Cys Gly Ser Gly Lys Asn Phe Pro Ser Pro Val Asp Ala Ala Phe Arg
1               5                   10                  15

<210> SEQ ID NO 9
<211> LENGTH: 4
<212> TYPE: PRT
<213> ORGANISM: Artificial Sequence
```

```
<220> FEATURE:
<223> OTHER INFORMATION: Synthetic Peptide

<400> SEQUENCE: 9

Gly Ser Gly Cys
1

<210> SEQ ID NO 10
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 10

Lys Gly Ser Gly Cys
1               5

<210> SEQ ID NO 11
<211> LENGTH: 354
<212> TYPE: PRT
<213> ORGANISM: Artificial Sequence
<220> FEATURE:
<223> OTHER INFORMATION: Synthetic Peptide

<400> SEQUENCE: 11

Met Ser Gly Ser His His His His His His Ser Gly Ile Glu Gly
1               5                   10                  15

Arg Gly Arg Leu Ile Lys His Met Thr Met Ala Lys Ala Thr Glu His
            20                  25                  30

Leu Ser Thr Leu Ser Glu Lys Asn Trp Gly Leu Ser Val Tyr Ala Asp
        35                  40                  45

Lys Pro Glu Thr Thr Lys Ile Leu Gly Gly His Leu Asp Ala Lys Asp
    50                  55                  60

Thr Val Gln Ile His Asp Ile Thr Gly Lys Thr Val Ile Gly Pro Asp
65                  70                  75                  80

Gly His Lys Gln Gly Phe Gly Asn Val Ala Thr Asn Thr Asp Gly Lys
                85                  90                  95

Glu Ile Gly Glu Leu Tyr Leu Pro Lys Thr Gly Leu Gln Glu Val Glu
            100                 105                 110

Val Lys Asp Asp Leu Tyr Val Ser Asp Ala Phe His Lys Ile Tyr His
        115                 120                 125

Ser His Ile Asp Ala Pro Lys Glu Thr Ala Ala Ser Leu Leu Gln Ala
    130                 135                 140

Gly Tyr Lys Ile Thr Gln Val Leu His Phe Thr Lys Phe Pro Glu Val
145                 150                 155                 160

Asp Val Leu Thr Lys Leu Gly Asn Gln Glu Pro Gly Gly Gln Thr Ala
                165                 170                 175

Leu Lys Leu Ser Ser Pro Ala Val Ile Thr Asp Lys Gln Trp Ala Gly
            180                 185                 190

Leu Val Glu Lys Ile Pro Pro Trp Glu Ala Pro Lys Leu Phe Leu Glu
        195                 200                 205

Pro Thr Gln Ala Asp Ile Ala Leu Leu Lys Ser His Ala Pro Glu Val
    210                 215                 220

Ile Thr Ser Ser Pro Leu Lys Ile Phe Tyr Asn Gln Gln Asn His Tyr
225                 230                 235                 240

Asp Gly Ser Thr Gly Lys Glu His Ser Ser Leu Ala Phe Trp Lys Val
                245                 250                 255
```

```
Ser Val Ser Gln Thr Ser Lys Glu Ser Asp Thr Ser Tyr Val Ser Leu
            260                 265                 270

Lys Trp Glu Leu Asp Leu Asp Ile Lys Ser Thr Val Leu Thr Ile Pro
        275                 280                 285

Glu Ile Ile Ile Lys Leu Ile Glu Asn Gly Tyr Phe His Pro Val Lys
    290                 295                 300

Ala Ser Tyr Pro Asp Ile Thr Gly Glu Lys Asp Pro Pro Ser Asp Leu
305                 310                 315                 320

Leu Leu Leu Lys Ala Leu Gln Asp Gln Leu Val Leu Val Ala Ala Lys
                325                 330                 335

Ala Glu Ile Glu Tyr Leu Glu Lys Gln Pro Gly Gly Ile Arg Gly Ser
            340                 345                 350

Gly Cys

<210> SEQ ID NO 12
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 12

Met Ser Gly Ser His His His His His His Ser Ser Gly Ile Glu Gly
1               5                   10                  15

Arg

<210> SEQ ID NO 13
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 13

Gly Arg Leu Ile Lys
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 14

His Met Thr Met Ala Lys
1               5

<210> SEQ ID NO 15
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 15

Ala Thr Glu His Leu Ser Thr Leu Ser Glu Lys
1               5                   10

<210> SEQ ID NO 16
<211> LENGTH: 15
<212> TYPE: PRT
<213> ORGANISM: Artificial Sequence
```

```
<220> FEATURE:
<223> OTHER INFORMATION: Synthetic Peptide

<400> SEQUENCE: 16

Asn Trp Gly Leu Ser Val Tyr Ala Asp Lys Pro Glu Thr Thr Lys
1               5                   10                  15

<210> SEQ ID NO 17
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 17

Ile Leu Gly Gly His Leu Asp Ala Lys
1               5

<210> SEQ ID NO 18
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 18

Asp Thr Val Gln Ile His Asp Ile Thr Gly Lys
1               5                   10

<210> SEQ ID NO 19
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 19

Thr Val Ile Gly Pro Asp Gly His Lys
1               5

<210> SEQ ID NO 20
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 20

Gln Gly Phe Gly Asn Val Ala Thr Asn Thr Asp Gly Lys
1               5                   10

<210> SEQ ID NO 21
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 21

Glu Ile Gly Glu Leu Tyr Leu Pro Lys
1               5

<210> SEQ ID NO 22
<211> LENGTH: 9
<212> TYPE: PRT
<213> ORGANISM: Artificial Sequence
<220> FEATURE:
```

<223> OTHER INFORMATION: Synthetic Peptide

<400> SEQUENCE: 22

Thr Gly Leu Gln Glu Val Glu Val Lys
1               5

<210> SEQ ID NO 23
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 23

Asp Asp Leu Tyr Val Ser Asp Ala Phe His Lys
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 24

Ile Tyr His Ser His Ile Asp Ala Pro Lys
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 25

Glu Thr Ala Ala Ser Leu Leu Gln Ala Gly Tyr Lys
1               5                   10

<210> SEQ ID NO 26
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 26

Ile Thr Gln Val Leu His Phe Thr Lys
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 27

Phe Pro Glu Val Asp Val Leu Thr Lys
1               5

<210> SEQ ID NO 28
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 28

Leu Gly Asn Gln Glu Pro Gly Gly Gln Thr Ala Leu Lys
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 29

Leu Ser Ser Pro Ala Val Ile Thr Asp Lys
1               5                   10

<210> SEQ ID NO 30
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 30

Gln Trp Ala Gly Leu Val Glu Lys
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 31

Ile Pro Pro Trp Glu Ala Pro Lys
1               5

<210> SEQ ID NO 32
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 32

Leu Phe Leu Glu Pro Thr Gln Ala Asp Ile Ala Leu Leu Lys
1               5                   10

<210> SEQ ID NO 33
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 33

Ser His Ala Pro Glu Val Ile Thr Ser Ser Pro Leu Lys
1               5                   10

<210> SEQ ID NO 34
<211> LENGTH: 15
<212> TYPE: PRT
<213> ORGANISM: Artificial Sequence
<220> FEATURE:
<223> OTHER INFORMATION: Synthetic Peptide

```
<400> SEQUENCE: 34

Ile Phe Tyr Asn Gln Gln Asn His Tyr Asp Gly Ser Thr Gly Lys
1               5                   10                  15

<210> SEQ ID NO 35
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 35

Glu His Ser Ser Leu Ala Phe Trp Lys
1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 36

Val Ser Val Ser Gln Thr Ser Lys
1               5

<210> SEQ ID NO 37
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 37

Glu Ser Asp Thr Ser Tyr Val Ser Leu Lys
1               5                   10

<210> SEQ ID NO 38
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 38

Trp Glu Leu Asp Leu Asp Ile Lys
1               5

<210> SEQ ID NO 39
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 39

Ser Thr Val Leu Thr Ile Pro Glu Ile Ile Ile Lys
1               5                   10

<210> SEQ ID NO 40
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 40
```

```
Leu Ile Glu Asn Gly Tyr Phe His Pro Val Lys
1               5                   10

<210> SEQ ID NO 41
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 41

Leu Ile Glu Asn Gly Tyr Phe His Pro Val Lys
1               5                   10

<210> SEQ ID NO 42
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 42

Asp Pro Pro Ser Asp Leu Leu Leu Leu Lys
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 43

Ala Leu Gln Asp Gln Leu Val Leu Val Ala Ala Lys
1               5                   10

<210> SEQ ID NO 44
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 44

Ala Glu Ile Glu Tyr Leu Glu Lys
1               5

<210> SEQ ID NO 45
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 45

Gln Pro Gly Gly Ile Arg
1               5
```

MASS SPECTROMETRIC ASSAYS FOR PEPTIDES

CROSS REFERENCE TO RELATED APPLICATIONS

This application is a National Stage Application of International Application No. PCT/US2011/028569, filed Mar. 15, 2011, which claims the benefit of U.S. patent application 61/314,149, entitled "MS Internal Standards at Clinical Levels" filed on Mar. 15, 2010 and U.S. patent application 61/314,154, entitled "Stable Isotope Labeled Peptides on Carriers" filed on Mar. 15, 2010; the disclosures of each of which are herein incorporated by reference in their entirety.

The disclosures of U.S. patent application Ser. No. 10/676,005, entitled High Sensitivity Quantitation of Peptides by Mass Spectrometry; filed 2 Oct. 2003; Ser. No. 60/415,499, entitled Monitor Peptide Enrichment Using Anti-Peptide Antibodies, filed 3 Oct. 2002; Ser. No. 60/420,613, entitled Optimization of Monitor Peptide Enrichment Using Anti-Peptide Antibodies, filed 23 Oct. 2002; Ser. No. 60/449,190, entitled High Sensitivity Quantitation of Peptides by Mass Spectrometry, filed 20 Feb. 2003; Ser. No. 60/496,037, entitled Improved Quantitation of Peptides by Mass Spectrometry, filed 18 Aug. 2003; Ser. No. 60/557,261, entitled Selection of Antibodies and Peptides for Peptide Enrichment, filed 29 Mar. 2004; Ser. No. 11/256,946, entitled Process For Treatment Of Protein Samples, filed 25 Oct. 2005, describing methods for processing protein samples imbibed within a porous membrane; Ser. No. 12/042,931, entitled Magnetic Bead Trap and Mass Spectrometer Interface"; and Ser. No. 11/147,397, entitled Stable Isotope Labeled Polypeptide Standards for Protein Quantitation" describing means for production of labeled peptide internal standards as recombinant concatamer proteins filed 8 Jun. 2005, are each herein incorporated by reference in their entireties.

U.S. Pat. No. 6,649,419, entitled Method and Apparatus for Protein Manipulation, filed 28 Nov. 2000, describing methods of eluting analytes captured on magnetic beads is herein incorporated by reference in their entireties.

BACKGROUND

Methods of using mass spectrometry for the measurement of established and candidate biomarker proteins could benefit from improvements in methods for the preparation, handling and quantitative performance of stable isotope labeled peptides. Such labeled peptides are used as internal standards in the analysis of peptides samples, including protein sample digests, by mass spectrometry. In a specific case, the art could benefit from improvements to the performance of the technology called "SISCAPA" that was disclosed in one or more of the patent filings referenced above, and a number of recent publications including, for instance: *An effective and rapid method for functional characterization of immunoadsorbents using POROS® beads and flow cytometry*, N. Leigh Anderson et al., Journal of Proteome Research 3:228-34 (2004); *Mass Spectrometric Quantitation of Peptides and Proteins Using Stable Isotope Standards and Capture by Anti-Peptide Antibodies (SISCAPA)*, Anderson, N. L. et al., Journal of Proteome Research 3: 235-44 (2004); *Anti-peptide antibody screening: selection of high affinity monoclonal reagents by a refined surface plasmon resonance technique*, Matthew E. Pope et al., J. Immunol. Methods, 341(1-2):86-96 (2009); *A Human Proteome Detection and Quantitation Project: hPDQ*, N. Leigh Anderson, et al., Mol. Cell. Proteomics 8:883-886 (2009); *SISCAPA Peptide Enrichment on Magnetic Beads Using an Inline Beadtrap Device*, N. Leigh Anderson, et al., Mol. Cell. Proteomics 8:995-1005 (2009); *An automated and multiplexed method for high throughput peptide immunoaffinity enrichment and multiple reaction monitoring mass spectrometry-based quantification of protein biomarkers*, Jeffrey R. Whiteaker, et al., Mol. Cell. Proteomics 9:184-196 (2010); *Proteomic-Based Multiplex Assay Mock Submissions: Supplementary Material to A Workshop Report by the NCI-FDA Interagency Oncology Task Force on Molecular Diagnostics*, Fred E. Regnier, et al., Clin. Chem. 56:2 165-171 (2010); *MALDI Immunoscreening (MiSCREEN): A Method for Selection of Anti-peptide Monoclonal Antibodies for Use in Immunoproteomics*, Morteza Razavi, Matthew E. Pope, Martin V. Soste, Brett A. Eyford, N. Leigh Anderson and Terry W. Pearson, Journal of Immunological Methods 364:50-64 (2011).

SUMMARY

Quantitative assays for evaluation of proteins in complex samples are provided, including assays of clinical specimens such as human plasma and other proteinaceous samples (including for example tissues, secretions, and body fluids of all living things, as well as samples prepared from heterogeneous mixtures of these), and specifically to the generation and use of stable isotope labeled peptides as Stable Isotope Standards (SIS) in assays based on mass spectrometric readouts.

Internal standards are provided, against which clinically important proteins and peptides derived from them by digestion can be compared. The internal standards are added to test samples at known concentrations that can, for example, be equivalent to clinical decision levels for the respective analytes, thereby facilitating interpretation of test results through the direct comparison of analyte amount with the amount of an internal standard as measured by a mass spectrometer (e.g., as peptide signal peak height or peak area). One internal standard suffices in a case where a single threshold ("test cutoff") value is used in result interpretation (e.g., in measurements of prostate specific antigen), while two internal standards may be used where a normal range is used with upper and lower bounds (one standard provided at the lower bound concentration and the other at the higher bound concentration). Using internal standards in this manner enables simplified test interpretation. The approach can be generalized to provide internal standards set to personalized reference values, allowing precise comparison of an individual to his/her own historical reference value or range. The approach may also use 2, 3, 4, 5, 6 or more internal standards at different concentrations, wherein at least one standard is present at the threshold value used for results interpretation where a single threshold ("test cutoff") value is used in result interpretation. Alternatively, the approach may also employ 3, 4, 5, 6 or more internal standards at different concentrations, wherein standards are present at the upper and lower threshold values used for results interpretation where a normal range is used with upper and lower bounds.

The technology also provides methods for the production, purification, characterization and use of stable-isotope-labeled peptide sequences which can be used together or separately as internal standards in the mass spectrometric quantitation of peptides and proteins. Briefly, one or more monitor peptide sequences (the "analytes") are selected to represent each protein to be measured. In the case of trypsin cleavage of the analyte-containing sample, candidate monitor peptides will be tryptic peptides (i.e., generally ending in K or R). A set of selected monitor peptide sequences representing multiple protein analytes can then be synthesized, each with a sequence extension that: 1) provides a chemical linkage site capable of joining the peptide to a large molecule "carrier"; and 2) establishes a proteolytic enzyme cleavage site within the peptide such that cleavage at the site releases from the carrier a labeled peptide of the same sequence as the intended analyte peptide. Stable isotopes (particularly $^{15}$N or $^{13}$C isotopically-enriched to >98% isotopic purity, but also $^{2}$H, $^{18}$O and any other stable isotopes of elements independently present in proteins) can be incorporated during synthesis by chemical means, in which case the stable isotopes are each independently incorporated at >95%, 96%, >97% or >98% substitution for a natural isotope at specific positions in the structure of amino acids or their analogous peptide synthesis precursors. Stable isotopes can also be incorporated into peptides by in vivo or in vitro means, in which case an organism or an in vitro translation system can be supplied with metabolic precursors or amino acids labeled at >95%, 96%, >97% or >98% isotopic substitution to achieve a highly substituted peptide product.

One or more labeled peptides can be covalently linked via chemical linkage to a carrier molecule such as keyhole limpet hemocyanine (KLH) to provide a stable, easily quantitated source of labeled peptide. The resulting "carrierSIS" molecule is substantially more easily handled than the labeled peptide alone, in part because it is highly soluble even after binding of many copies of the SIS peptide and thus is less likely to stick to surfaces of storage vials, pipettes, etc., than is a free SIS peptide. The carrierSIS protein can be purified using specific tags incorporated into the carrier molecule (e.g., peptide or biotin tags) or based on physical properties such as solubility or size (i.e., on an SDS electrophoresis gel). The intact carrierSIS protein can be quantitated once by amino acid analysis, which together with a knowledge of the quantity of bound SIS peptide yields a molar concentration that applies to SIS peptides subsequently liberated by proteolysis.

The carrierSIS protein can be added at known amounts to complex protein samples prior to proteolytic digestion, and digested with the sample proteins to produce a series of SIS peptides whose stoichiometry to one another is known, and whose absolute concentration is also known. Alternatively the carrier in the carrierSIS can be a particle containing non-protein components (e.g., a magnetic bead). In use the carrierSIS can be digested with the sample to liberate SIS peptide or pre-digested to yield a stoichiometric mixture of SIS peptides to be added to a sample before or after sample digestion. These SIS peptides are then used as standards for quantitation of sample protein derived peptides by mass spectrometry (e.g., as in the SISCAPA method disused in U.S. Pat. No. 7,632,686, entitled "High Sensitivity Quantitation of Peptides by Mass Spectrometry"). The carrierSIS construct provides an alternative to the previously disclosed recombinant method for producing SIS-containing concatamer proteins (U.S. patent application Ser. No. 11/147,397 "Stable Isotope Labeled Polypeptide Standards for Protein Quantitation").

BRIEF DESCRIPTION OF THE DRAWINGS

FIG. 7. Linkage of a polySIS peptide to an activated carrier and release of SIS peptides by tryptic digestion. The sequence of the polySIS is described in detail as Seq ID No. 39 in U.S. patent application Ser. No. 11/147,397. Part A shows the extension sequences GSGC SEQ ID No. 9 that can be linked to a carrier (41) by an optional spacer (42) that has a carrier linkage site denoted "M" (43), along with the polySIS sequence (46) that may bear carboxyl terminal extension sequence (45) having a terminal cysteine (44):

SEQ ID No. 11

MSGSHHHHHHSSGIEGRGRLIKHMTMAKATEHLSTLSEKNWGLSVYADKPETTKILGGHLDAK

DTVQIHDITGKTVIGPDGHKQGFGNVATNTDGKEIGELYLPKTGLQEVEVKDDLYVSDAFHKIY

HSHIDAPKETAASLLQAGYKITQVLHFTKFPEVDVLTKLGNQEPGGQTALKLSSPAVITDKQWA

GLVEKIPPWEAPKLFLEPTQADIALLKSHAPEVITSSPLKIFYNQQNHYDGSTGKEHSSLAFWKVS

VSQTSKESDTSYVSLKWELDLDIKSTVLTIPEIIIKLIENGYFHPVKASYPDITGEKDPPSDLLLLKA

Figure 1:
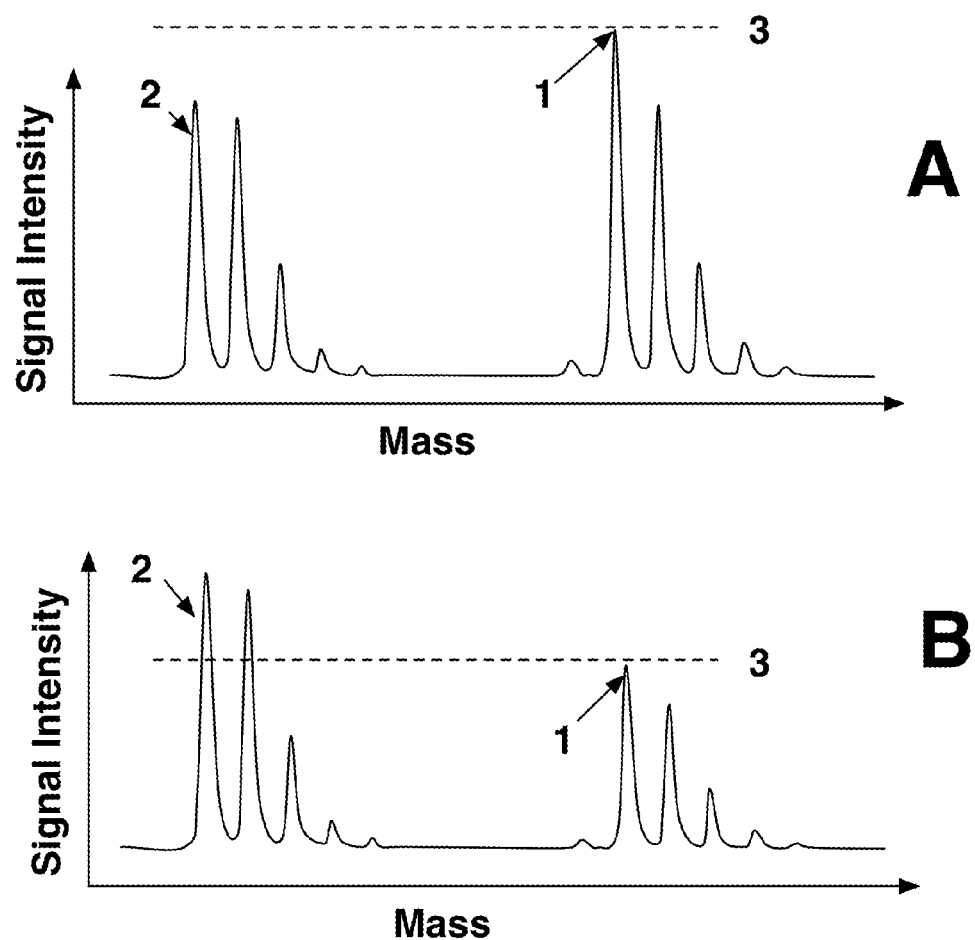
FIG. 1. Comparison of analyte and internal standard peptides by MALDI-MS. Internal standard 1 is present in an amount such that its signal level 3 indicates the clinical decision point for the endogenous analyte 2.

LQDQLVLVAAKAEIEYLEKQPGGIRGSGC,;

Part B, shows the polySIS sequences including extension sequences (47) that are bound to the carrier.

Part C shows a collection of the peptides (48) released following proteolytic treatment of the carrier leaving the extension sequence (where one is employed) attached to the carrier in this example.

| MSGSHHHHHHSSGIEGR,; | SEQ ID No. 12 |
|---|---|
| GRLIK,; | SEQ ID No. 13 |
| HMTMAK,; | SEQ ID No. 14 |
| ATEHLSTLSEK,: | SEQ ID No. 15 |
| NWGLSVYADKPETTK,; | SEQ ID No. 16 |

```
ILGGHLDAK,;              SEQ ID No. 17

DTVQIHDITGK,;            SEQ ID No. 18

TVIGPDGHK,;              SEQ ID No. 19

QGFGNVATNTDGK,;          SEQ ID No. 20

EIGELYLPK,;              SEQ ID No. 21

TGLQEVEVK,;              SEQ ID No. 22

DDLYVSDAFHK,;            SEQ ID No. 23

IYHSHIDAPK,;             SEQ ID No. 24

ETAASLLQAGYK,;           SEQ ID No. 25

ITQVLHFTK,;              SEQ ID No. 26

FPEVDVLTK,;              SEQ ID No. 27

LGNQEPGGQTALK,;          SEQ ID No. 28

LSSPAVITDK,;             SEQ ID No. 29

QWAGLVEK,;               SEQ ID No. 30

IPPWEAPK,;               SEQ ID No. 31

LFLEPTQADIALLK,;         SEQ ID No. 32

SHAPEVITSSPLK,;          SEQ ID No. 33

IFYNQQNHYDGSTGK,;        SEQ ID No. 34

EHSSLAFWK,;              SEQ ID No. 35

VSVSQTSK,;               SEQ ID No. 36

ESDTSYVSLK,;             SEQ ID No. 37

WELDLDIK,;               SEQ ID No. 38

STVLTIPEIIIK,;           SEQ ID No. 39

LIENGYFHPVK,;            SEQ ID No. 40

ASYPDITGEK,;             SEQ ID No. 41

DPPSDLLLLK,;             SEQ ID No. 42

ALQDQLVLVAAK,;           SEQ ID No. 43

AEIEYLEK,;               SEQ ID No. 44
and

QPGGIR,;                 SEQ ID No. 45
```

DETAILED DESCRIPTION

The term "amount", "concentration" or "level" of an analyte or internal standard means the physical quantity of the substance referred to, either in terms of mass (or equivalently moles) or in terms of concentration (the amount of mass or moles per volume of a solution or liquid sample).

The term "analyte" or "ligand" may be any of a variety of different molecules, or components, pieces, fragments or sections of different molecules that are to be measured or quantitated in a sample. An analyte may thus be a protein, a peptide derived from a protein by digestion or other fragmentation technique, a small molecule (such as a hormone, a metabolite, a drug, a drug metabolite) or nucleic acids (DNA, RNA, and fragments thereof produced by enzymatic, chemical or other fragmentation processes).

The term "antibody" means a monoclonal or monospecific polyclonal immunoglobulin protein such as IgG or IgM. An antibody may be a whole antibody or antigen-binding antibody fragment derived from a species (e.g., rabbit or mouse) commonly employed to produce antibodies against a selected antigen, or may be derived from recombinant methods such as protein expression, and phage/virus display. See, e.g., U.S. Pat. Nos. 7,732,168; 7,575,896; and 7,431927, which describe preparation of rabbit monoclonal antibodies. Antibody fragments may be any antigen-binding fragment that can be prepared by conventional protein chemistry methods or may be engineered fragments such as scFv, diabodies, minibodies and the like. It will be understood that other classes of molecules such as DNA and RNA aptamers configured as specific and high affinity binding agents may, be used as alternatives to antibodies or antibody fragments in appropriate circumstances.

The term "bind" or "react" means any physical attachment or close association, which may be permanent or temporary. Generally, reversible binding includes aspects of charge interactions, hydrogen bonding, hydrophobic forces, van der Waals forces etc., that facilitate physical attachment between the molecule of interest and the analyte being measuring. The "binding" interaction may be brief as in the situation where binding causes a chemical reaction to occur. Reactions resulting from contact between the binding agent and the analyte are also within the definition of binding for the purposes of the present technology, provided they can be later reversed to release a monitor fragment.

The term "binding agent" means a molecule or substance having an affinity for one or more analytes, and includes antibodies (for example polyclonal, monoclonal, single chain, and modifications thereof), aptamers (made of DNA, RNA, modified nucleotides, peptides, and other compounds), etc. "Specific binding agents" are those with particular affinity for a specific analyte molecule.

The terms "clinical evaluation threshold", "clinical decision point" and "test evaluation threshold" (which are used here interchangeably) mean a value of analyte abundance or concentration in a biological (including clinical) sample that serves as a decision point for a test result (typically a clinical test result). For example, a threshold of 4.1 ng/ml has been used as a clinical decision point in the interpretation of prostate specific antigen test results in men: values above this level indicate increased risk of prostate cancer, and below this level no action in typically taken. Alternatively for some analytes a value lower than the clinical decision point can be the indication of higher risk. Clinical decision points are typically derived from large clinical studies and represent a statistical parameter set by clinical researchers to provide a given specificity and sensitivity in answering a particular clinical question. Similarly, methods of risk analysis can be used to determine test evaluation thresholds in non-clinical situations, such as the determination of permitted levels of certain protein or peptide contaminants in foods, beverages, drugs, cosmetics, environmental and other samples required to address regulatory requirements in various countries. For use in a specific test it will be understood that a test evaluation threshold can be set based on results obtained using the specific test or an equivalent methodology, in order that any analytical biases inherent in the test be reflected in the threshold. Thus, if an MS-based assay detects a peptide obtained by tryptic digestion of a target protein in a sample, and for some reason the tryptic yield of this peptide is reproducible but not 100%, for example an 85% yield of peptide per protein on a molar basis, then a test evaluation threshold for this peptide in the example would be set a value equivalent to 85% of the amount of the corresponding protein in the sample, i.e., equal to the level of peptide analyte observed in the MS at the test evaluation threshold.

The terms "clinical reference range" and "clinical reference interval" mean the range of abundance or concentration values of an analyte that are deemed to be with the "normal" clinical range. Such ranges are frequently established by determination of analyte levels in a normal population, and the clinical reference range typically determined as the central 95% of the resulting histogram (with 2.5% of the population above and 2.5% below the resulting high and low values). As used here, these terms also refer to ranges whose bounds are defined by clinical features other than the distribution of results in normal individuals (e.g., the population reference range in diabetic patients), and clinical ranges based on a patient's prior test values for the same or other analytes, alone or in combination with population test data. A variety of statistical approaches can be used to calculate such ranges from analyte measurements, and this is advantageously can be done prior to their application in the design of an assay or the determination of an amount of internal standard to use in the assay. As in the case of a single test evaluation threshold, it will be understood that a clinical reference interval for use in a specific test can be set based on results obtained using the specific test or an equivalent methodology, in order that any analytical biases inherent in the test are reflected in the threshold.

The terms "clinical cutpoint panel" and "multi-threshold classifier" mean a set of two or more different threshold levels used to assess the result of an assay by comparing a measure of analyte amount with such threshold levels to determine whether analyte amount is higher than the highest threshold, lower than the lowest threshold, or between two particular threshold levels, and include clinical interpretive scales with more than two references values (e.g., a three point scale whose 4 segments indicate no, low, moderate or high risk).

The term "carrier linkage site" refers to a chemical grouping or moiety in a suitably prepared carrier molecule that is capable of reacting with a peptide linkage site in a modified or unmodified peptide molecule to yield a covalent or very tight non-covalent linkage between the peptide and the carrier. In one embodiment, the chemical linkage site is present within the extension to the SIS peptide.

The term "carrier molecule" refers to a molecule having multiple sites at which peptides can be attached, said attachment being either covalent or non-covalent but tight (e.g., via avidin-biotin interaction). Examples of carriers include proteins (e.g., activated KLH or albumin bearing multiple maleimide groups [e.g., Thermofisher Imject Maleimide-Activated Mariculture KLH] capable of reacting with multiple cysteine-containing SIS peptides), and other polymeric molecules having desirable properties such as solubility and stability, including for example dextrans, linear polyacrylamides, agarose, dendrimers, etc. Carrier molecules are typically larger than tryptic peptides, generally having molecular weights in the range 3,000 to 20,000,000. In some embodiments (e.g., polymer carriers) the carrier molecules will have molecular weights in a range: from about 3,000 to about 10,000, or from about 10,000 to about 100,000, or from about 100,000 to about 1,000,000, or from about 1,000,000 to about 5,000,000, or from about 5,000,000 to about 20,000,000 Daltons.

The term "carrier particle" means a physical particle having sites (e.g., single or multiple sites) at which peptides can be attached, said attachment being either covalent or non-covalent and of a kind such that the peptide may released from the particle at an appropriate point in the sample preparation workflow. Examples include agarose beads, magnetic beads, quantum dots, viruses, and particles of controlled-pore glass, chromatography media such as POROS or silica, and polystyrene. Carrier particles can be in the range of 10 nanometer to 1 millimeter in size. In some embodiments the carrier particles will have a size (e.g., average diameter) in a range: from about 10 to about 100, or from about 100 to about 10,000, or from about 10,000 to about 100,000, or from about 10,000 to about 1,000,000, or from about 100 to about 10,000, or from about 1,000 to about 100,000 nanometers.

The term "carrier surface" means a surface to which peptides can be attached, said attachment being either covalent or non-covalent and of a kind such that the peptide is released from the particle at the appropriate point in the sample preparation workflow. Examples include the surfaces (often the inner liquid-contacting surfaces) of vessels such as sample wells, pipette tips, cuvettes, or capillary tubes used in a sample processing workflow.

The term "carrier" means a carrier molecule, a carrier particle or a carrier surface.

The term "carrierSIS" or "conjugate" or "carrierSIS complex" or "SIS peptide delivery vehicle" means a carrier to which SIS peptides or extended SIS peptides are bound or linked.

The term "carrierPolySIS" or "conjugate" or "carrierPolySIS complex" or "polySIS peptide delivery vehicle" means a carrier to which polySIS peptides or extended polySIS peptides are bound or linked.

The term "denaturant" includes a range of chaotropic and other chemical agents that act to disrupt or loosen the 3-D structure of proteins without breaking covalent bonds, thereby rendering them more susceptible to proteolytic treatment. Examples include urea, guanidine hydrochloride, ammonium thiocyanate, trifluoroethanol and deoxycholate, as well as solvents such as acetonitrile, methanol and the like.

The term "electrospray ionization" (ESI) refers to a method for the transfer of analyte molecules in solution into the gas and ultimately vacuum phase through use of a combination of liquid delivery to a pointed exit and high local electric field.

The term "extended peptide" means a peptide having a subsequence that is the same as a peptide analyte and one or more additional subsequences and chemical moieties that provide additional functionality (such as attachment to a carrier) but are separated from the analyte subsequence by action of the proteolytic activity used to create a sample digest.

The term "extended SIS" means an extended peptide comprising a labeled peptide segment that is a SIS peptide.

The term "immobilized enzyme" means any form of enzyme that is fixed to the matrix of a support by covalent or non-covalent interaction such that the majority of the enzyme remains attached to the support of the membrane.

The term "magnet", "permanent magnet", or "electromagnet" are used here to mean any physical system, whether electrically powered or static, capable of generating a magnetic field.

The term "magnetic field" or "magnetic field gradient" are used here interchangeably, and refer to a physical region within which a spatially varying magnetic field exists.

The terms "magnetic particle" and "magnetic bead" are used interchangeably and mean particulate substances capable of carrying binding agents (whether attached covalently or non-covalently, permanently or temporarily) and which can respond to the presence of a magnetic field gradient by movement. The term includes beads that are referred to as paramagnetic, superparamagnetic, and diamagnetic.

The terms "particle" or "bead" mean any kind of particle in the size range between 10 nm and 1 cm, and includes magnetic particles and beads.

The term "MALDI" means Matrix Assisted Laser Desorption Ionization and related techniques such as SELDI, and includes any technique that generates charged analyte ions from a solid analyte-containing material on a solid support under the influence of a laser or other means of imparting a short energy pulse.

The term "Mass spectrometer" (or "MS") means an instrument capable of separating molecules on the basis of their mass m, or m/z where z is molecular charge, and then detecting them. In one embodiment, mass spectrometers detect molecules quantitatively. An MS may use one, two, or more stages of mass selection. In the case of multistage selection, some means of fragmenting the molecules is typically used between stages, so that later stages resolve fragments of molecules selected in earlier stages. Use of multiple stages typically affords improved overall specificity compared to a single stage device. Often, quantitation of molecules is performed in a triple-quadrupole mass spectrometer, but it will be understood herein that a variety of different MS configurations may be used to analyze the molecules described, and specifically MALDI instruments including MALDI-TOF, MALDI-TOF/TOF, and MALDI-TQMS and electrospray instruments including ESI-TQMS and ESI-QTOF, in which TOF means time of flight, TQMS means triple quadrupole MS, and QTOF means quadrupole TOF.

The term "monitor fragment" may mean any piece of an analyte up to and including the whole analyte that can be produced by a reproducible fragmentation process (or without a fragmentation if the monitor fragment is the whole analyte) and whose abundance or concentration can be used as a surrogate for the abundance or concentration of the analyte. The term "monitor peptide" or "target peptide" means a peptide chosen as a monitor fragment of a protein or peptide.

The terms "multiplex clinical thresholds" or "multiplex test thresholds" mean a series of test values of analyte abundance or concentration in a biological (including clinical) sample that serve as decision points for a series of individual analyte measurements carried out as a single test procedure (i.e., in a multiplex format). In the simplest case, a specific test evaluation threshold is provided for each analyte in the panel, and the result of the multiplex test is determined by an algorithm taking into account which analytes exceed and which do not exceed their respective thresholds.

The term "Natural" or "Nat" means the form of such a peptide that is derived from a natural biological sample by proteolytic digestion, and thus, contains approximately natural abundances of elemental isotopes. Nat peptides typically do not contain appreciable amounts of a stable isotope label such as is intentionally incorporated in SIS internal standards.

The term "personal reference level" and "personal reference range" refer to the use of analyte levels established previously for an individual patient in the interpretation of test results.

The term "peptide-carrier conjugate" means a carrier with peptide(s) linked to it through bond(s) between carrier linkage site(s) and peptide linkage site(s).

The term "peptide linkage site" refers to a chemical grouping or moiety in a modified or unmodified peptide molecule that is capable of reacting with a carrier linkage site in a suitably prepared carrier molecule to yield a covalent or very tight non-covalent linkage between the peptide and the carrier. In one embodiment, the chemical linkage site is present within the extension to the SIS peptide.

The term polySIS means a protein or peptide comprising subsequences identical to monitor peptides representing two or more different proteins in sequence contexts such that the monitor peptides are released by proteolytic digestion.

The term "proteolytic enzyme cleavage site" refers to a site within an extended SIS peptide sequence at which the chosen proteolytic treatment (typically an enzyme such as trypsin) cleaves the extended SIS sequence, releasing peptides fragments (typically two) of which one is the SIS peptide sequence (identical to the analyte, or Nat, sequence for which the SIS serves as an internal standard).

The term "proteolytic treatment" or "enzyme" may refer any of a large number of different enzymes, including trypsin, chymotrypsin, lys-C, v8 and the like, as well as chemicals, such as cyanogen bromide. In this context, a proteolytic treatment acts to cleave peptide bonds in a protein or peptide in a sequence-specific manner, generating a collection of shorter peptides (a digest).

The term "sample" means any complex biologically-generated sample derived from humans, other animals, plants or microorganisms, or any combinations of these sources. "Complex digest" means a proteolytic digest of any of these samples resulting from use of a proteolytic treatment.

The terms "SIS", "stable isotope standard" and "stable isotope labeled version of a peptide or protein analyte" mean a peptide or protein, such as a peptide or protein having a unique sequence that is identical or substantially identical to that of a selected peptide or protein analyte, and including a label of some kind (e.g., a stable isotope) that allows its use as an internal standard for mass spectrometric quantitation of the natural (unlabeled, typically biologically generated) version of the analyte (see U.S. Pat. No. 7,632,686 "High Sensitivity Quantitation of Peptides by Mass Spectrometry"). In one embodiment, a SIS peptide or protein comprises a peptide sequence that has a structure that is chemically identical to that of the molecule for which it will serve as a standard, except that it has isotopic labels at one or more positions that alter its mass. Hence a SIS is 1) recognized as equivalent to the analyte in a pre-analytical workflow, and is not appreciably differentially enriched or depleted compared to the analyte prior to mass spectrometric analysis, and 2) differs from it in a manner that can be distinguished by a mass spectrometer, either through direct measurement of molecular mass or through mass measurement of fragments (e.g., through MS/MS analysis), or by another equivalent means. Stable isotope standards include peptides having non-material modifications of this sequence, such as a single amino acid substitution (as may occur in natural genetic polymorphisms), substitutions (including covalent conjugations of cysteine or other specific residues), or chemical modifications (including glycosylation, phosphorylation, and other well-known post-translational modifications) that do not materially affect enrichment or depletion compared to the analyte prior to mass spectrometric analysis. In one embodiment, SIS are those in which the level of substitution of each stable isotope (e.g., $^{13}C$, $^{15}N$, $^{18}O$ or $^{2}H$) at the specific sites within the peptide structure where the isotope(s) is/are incorporated (i.e., those sites that depart significantly from the natural unenriched isotope distribution) is/are >95%, >96%, >97%, or >98%.

The term "SISCAPA" means the method described in U.S. Pat. No. 7,632,686, entitled High Sensitivity Quantitation of Peptides by Mass Spectrometry and in Mass Spectrometric Quantitation of Peptides and Proteins Using Stable Isotope Standards and Capture by Anti-Peptide Antibodies (SIS-CAPA). Anderson, N. L., Anderson, N. G., Haines, L. R., Hardie, D. B., Olafson. R. W., and Pearson, T. W, Journal of Proteome Research 3: 235-44 (2004).

The term "small molecule" or "metabolite" means a multi-atom molecule other than proteins, peptides and DNA; the term can include but is not limited to amino acids, steroid and other small hormones, metabolic intermediate compounds, drugs, drug metabolites, toxicants and their metabolites, and fragments of larger biomolecules.

The term "stable isotope" means an isotope of an element naturally occurring or capable of substitution in proteins or peptides that is stable (does not decay by radioactive mechanisms) over a period of a day or more. The primary examples of interest in this context are $^{13}C$, $^{15}N$, $^{2}H$, and $^{18}O$, of which the most commonly used are $^{13}C$ and $^{15}N$.

The term "standardized sample" means a protein or peptide sample to which stable isotope labeled version(s) of one or more peptide or protein analytes have been added at levels corresponding to test evaluation thresholds to serve as internal standards.

The following embodiments of the present technology make use of a series of concepts described in this specification. These concepts provide background as to specific embodiments of the methods and compositions described herein.

1 The SISCAPA Method

SISCAPA assays combine affinity enrichment of specific peptides with quantitative measurement of those peptides by mass spectrometry. In order to detect and quantitatively measure protein analytes, the SISCAPA technology makes use of anti-peptide antibodies (or any other binding entity that can reversibly bind a specific peptide sequence of about 5-20 residues) to capture specific peptides from a mixture of peptides, such as that arising, for example, from the specific cleavage of a protein mixture (like human serum or a tissue lysate) by a proteolytic enzyme such as trypsin or a chemical reagent such as cyanogen bromide. By capturing a specific peptide through binding to an antibody (the antibody being typically coupled to a solid support either before or after peptide binding), followed by washing of the antibody:peptide complex to remove unbound peptides, and finally elution of the bound peptide into a small volume (typically achieved by an acid solution such as 5% acetic acid), the SISCAPA technology makes it possible to enrich specific peptides that may be present at low concentrations in the whole digest, and therefore undetectable in simple mass spectrometry (MS) or liquid chromatography-MS (LC/MS) systems against the background of more abundant peptides present in the mixture. It also provides a sample that is less complex, and therefore exhibits lesser 'matrix effects' and fewer analytical interferences, than observed in the starting digest. This in turn permits mass spectrometry analysis without further separation steps, although additional separation processes could be used if desired. The sample can be concentrated prior to analysis if necessary, but this concentration does not provide any further analyte peptide separation. This enrichment step is intended to capture peptides of high, medium or low abundance and present them for MS analysis: it therefore discards information as to the relative abundance of a peptide in the starting mixture in order to boost detection sensitivity. This abundance information, which is of great value in the field of proteomics, can be recovered, however, through the use of isotope dilution methods: the SISCAPA technology makes use of such methods (e.g., by using stable isotope labeled versions of target peptides) in combination with specific peptide enrichment, to provide a method for quantitative analysis of peptides, including low-abundance peptides.

The approach to standardization in SISCAPA is to create a version of the peptide to be measured which incorporates one or more stable isotopes of mass different from the predominant natural isotope, thus forming a labeled peptide variant that is chemically identical (or nearly-identical) to the natural peptide present in the mixture, but which is nevertheless distinguishable by a mass spectrometer because of its altered peptide mass due to the isotopic label(s). In one embodiment, the method for creating the labeled peptide is chemical synthesis, wherein a peptide with chemical structure identical to the natural analyte can be made while incorporating amino acid precursors that contain heavy isotopes of hydrogen, carbon, oxygen or nitrogen (e.g., $^{2}H$, $^{13}C$, $^{18}O$ or $^{15}N$) to introduce the isotopic label. In theory one could also use radioactive (i.e., unstable) isotopes (such as $^{3}H$), but this is less attractive for safety reasons. The isotopic peptide variant (a Stable Isotope-labeled Standard, or SIS) is used as an internal standard and is added to the sample peptide mixture at a known concentration before enrichment by antibody capture. The antibody captures and enriches both the natural and the labeled peptide together (having no differential affinity for either) according to their relative abundances in the sample. Since the labeled peptide is added at a known concentration, the ratio between the amounts of the natural and labeled forms detected by the final MS analysis allows the concentration of the natural peptide in the sample mixture to be calculated. Thus, the SISCAPA technology makes it possible to measure the quantity of a peptide of low abundance in a complex mixture, and since the peptide is typically produced by quantitative (complete) cleavage of sample proteins, the abundance of the parent protein in the mixture of proteins can be deduced. The SISCAPA technology can be multiplexed to cover multiple peptides measured in parallel, and can be automated through computer control to afford a general system for protein measurement. Creating a new protein-specific assay thus, requires only that a peptide-specific antibody and a labeled peptide analog be created. A feature of the SISCAPA technology is directed at establishing quantitative assays for specific proteins selected a priori, rather than at the problem of comparing all of the unknown components of two or more samples to one another. It is this focus on specific assays that makes it attractive to generate specific antibodies to each monitor peptide (in principle one antibody binding one peptide for each assay). Prior to the development of SISCAPA it was believed that anti-peptide antibodies were neither sufficiently specific nor had sufficient affinity to allow isolation of a single peptide from a complex digest. Previously described methods have not focused on anti-peptide antibodies, but used instead general affinity concepts that would bind and enrich all of a class of peptides by recognizing a ligand, label or feature common to the class: e.g., immobilized metal affinity chromatography (IMAC) to select phosphopeptides as a group, anti-phosphotyrosine antibodies to select phosphotyrosine-containing peptides as a group, or lectins to select glycopeptides as a group. The SISCAPA technology provides a means to enrich each peptide sequence specifically with a different antibody (or other equivalently selective binding reagent).

An alternative to using SIS peptides is to use multiple copies of SIS peptides arranged as a linear polypeptide strand known as polySIS peptides. PolySIS peptides have been described, for example, in U.S. patent application Ser. No. 11/147,397 and may be prepared chemically, in vitro or in vivo using the same techniques used for SIS peptides. Poly-SIS peptides may also be prepared in "extended SIS" form and coupled to a carrier in the same fashion that SIS peptides or extended SIS peptides are attached. In one embodiment polySIS polypeptides comprise a repeat of a single peptide that may be used as a monitor peptide. In another embodiment, polySIS polypeptides (which may also be termed polySIS proteins) have an amino acid sequence containing several (at least two, three, four, five or more) amino acid subsequences found in nature and wherein at least two different subsequences act as monitor sequences. In such an embodiment, the subsequences of the polySIS polypeptide are part of at least one (or alternatively two, three, four, five or more) natural proteins that is/are target protein(s) whose levels will be assessed. The subsequences of polySIS peptides contain at their ends cleavage sites that can be cleaved by the same site-specific proteolytic treatment to release said subsequences from the native proteins in the test sample. Thus, polySIS peptides may be used as an internal standard in the same fashion as SIS peptides and also as a single internal standard for multiple protein analytes, wherein the ratio of the monitor peptide sequences will be fixed by the number of times the subsequence appears in the polySIS peptide.

A further objective of SISCAPA is to deliver a series of different monitor peptides (selected by a corresponding series of specific antibodies and potentially derived by digestion of different sample proteins) to a mass spectrometer at very nearly the same abundance (e.g., within a factor of 500, 250, 200, 100, 50, 20, or 10 fold molar abundance) and free of other extraneous peptides. By equalizing the abundance of a series of peptides through antibody capture of a selectable fraction of each peptide, the method can ensure that all the captured peptides are present within the mass spectrometer's dynamic range and that this dynamic range can be optimally employed in spanning the true dynamic range of the peptide analytes. If the MS system has a dynamic range of 1000 (a range of 100 to 10,000 is typical depending on the type of MS), the method attempts to ensure that the peptides of interest are presented to the MS at a level in the middle of that range, thus, allowing an optimal capacity to detect increases or decreases in relative abundance of the natural and isotopically labeled forms. If the peptides were presented to the MS at different abundances (e.g., those peptides at relative concentrations of 1, 0.001 and 1,000), then the MS will have great difficulty in detecting equivalent quantitative differences between natural and isotopically labeled forms of these three peptides. By "flattening" the abundance distribution of the peptides the quantitative resolution is substantially enhanced.

The basic SISCAPA embodiment combines 1) methods for creation and affinity purification of antibodies that tightly but reversibly bind short peptide sequences; 2) methods for digestion of complex protein mixtures to yield short peptides; 3) methods for synthesis of defined peptides containing isotopic labels; 4) methods for efficient capture and release of peptides; and 5) methods for MS measurement of ratios of labeled and unlabeled (sample-derived) peptides to yield a quantitative measurement.

In the simplest SISCAPA embodiment, the following steps are carried out for each protein to be measured in plasma (or another sample containing protein(s)) in order to generate a specific quantitative assay system. The starting point is protein identification, which typically is based on the sequence of known proteins identified by accession number in a sequence database such as SwissProt or Genbank. The steps include one or more of:

Selecting a Monitor Peptide (Step a)

Using the known sequence of the protein, one or more peptide segments within the protein are selected as "monitor peptides." A good monitor peptide satisfies a set of criteria designed to select peptides that can be chemically synthesized with high yield, that can be detected quantitatively in an appropriate mass spectrometer, that are reproducibly cleaved from the parent protein during digestion, and that elicit antibodies when used as antigens, although any peptide resulting from cleavage with the desired enzyme is a possible choice. One useful set of criteria is the following:

i: The peptide has a sequence that results from cleavage of the protein with a desired proteolytic enzyme (e.g., trypsin). All the candidate tryptic peptides can be easily computed from the protein sequence by application of generally available software.

ii: The peptide should be hydrophilic overall, and soluble in conventional solvents used in enzymatic digestion and affinity chromatography. Hydrophilic peptides can be selected based on computed scores obtained for each peptide from generally available software programs. In general the hydrophilic peptides are those that contain more polar amino acids (his, lys, arg, glu, asp) and fewer hydrophobic amino acids (trp, phe, val, leu, ile).

iii: The peptide should contain a) no cys, because a c-terminal cys may be added for convenience in conjugation of the immunogen (the presence of two cys in a peptide can lead to undesirable dimerization and cross-linking) and because the alkylation of peptide cysteines can be irreproducible; and b) no met, because of the possibility of oxidation of this amino acid.

iv: The peptide should ionize well by either electrospray (ESI) or matrix-assisted laser desorption (MALDI) ionization. This characteristic can be estimated by software programs or determined experimentally by MS analysis of a digest of the protein in question to see which peptides are detected at highest relative abundance.

v: The peptide should be immunogenic in the species in which the antibody will be raised. Immunogenicity is generally better for peptides that are hydrophilic (compatible with (ii) above); that include a bend predicted by secondary structure prediction software; that include no glycosylation sites; and that are 10-20 amino acids in length.

vi: The peptide should not include within it the sites of any common sequence polymorphisms (i.e., genetic variants) in the target protein (as this could affect the estimation of the respective protein's abundance if the variant peptide does not appear at the expected mass).

vii: the peptide should not share appreciable homology with any other protein of the target organism (as determined for example by the BLAST sequence comparison program). This characteristic should tend to reduce any interference in the antibody capture step from peptides originating in proteins other than the target.

viii: the peptide should be produced at reproducible (ideally high, close to 100%) stoichiometric yield by tryptic (or other) digestion of the starting sample.

ix: the peptide and its fragments measured by mass spectrometry (e.g., by selected or multiple reaction monitoring using a triple quadrupole MS) should produce comparable results at multiple analysis sites and on different mass spectrometers (i.e. yielding good site to site reproducibility).

All possible peptides derived from the target protein can be evaluated according to these criteria, either through computation or experimental analysis of digests of isolated target proteins or biological samples including the target protein, and one or more peptides selected that best balance the requirements of the method. A database of all the peptides (e.g., tryptic peptides) and their derived properties for a finite set of analytes such as the known proteins in plasma can be created and used as a basis for selection of monitor peptides. Beginning with the known amino acid sequences of protein analytes, efficient algorithms can construct all the possible tryptic peptides that will be created by trypsin digestion of the protein. These tryptic peptide sequences can be stored as records in a database, and similar records generated for other possible cleavage enzymes and reagents. Additional algorithms can be employed to compute various physical and biological properties of each peptide, including length, mass, net charge at neutral pH, propensity to adopt secondary structure, hydrophilicity, etc. These derived data can be tabulated for each peptide, and additional aggregate calculations performed to develop prioritizing scores associated with likelihood of success as a monitor peptide. These priority scores can be sorted to select candidate monitor peptides for each protein.

Creating Isotope-Labeled Monitor Peptides (Step b)

An isotopically labeled version of the selected peptide (a "SIS") is then made in which the chemical structure is maintained, but one or more atoms are substituted with an isotope such that an MS can distinguish the labeled peptide from the normal peptide (containing the natural abundance of each element's isotopes). For example, nitrogen-15 or carbon-13 could be introduced instead of the natural nitrogen-14 or carbon-12 at one or more positions in the synthesized peptide. The synthesized peptide will be heavier by a number of atomic mass units equal to the number of substituted nitrogens or carbons. The peptide is carefully made so that the number of added mass units is known and well-determined (i.e., all of the material produced as one standard has the same mass insofar as possible—achieved by using highly enriched isotopic variants of the amino acids, for example). In one embodiment, nitrogen-15 or carbon-13 labeled amino acid precursors substituted at >98% are used at one or more positions in the peptide synthesis process to introduce between 4 and 10 additional mass units compared to the natural peptide. Such nitrogen-15 labeled amino acid precursors (or their carbon-13 labeled equivalents) are commercially available as FMOC derivatives suitable for use directly in conventional commercial peptide synthesis machines. The resulting labeled monitor peptides can be purified using conventional LC methods (typically to >90% purity) and characterized by MS to ensure the correct sequence and mass.

Creating Anti-Peptide Antibodies (Step c)

To immunize an animal for production of anti-peptide antibodies, the same peptide (labeled or not, if the latter is, as expected, more economical) is coupled to a carrier protein (e.g., keyhole limpet hemocyanine (KLH); not homologous to a human protein) and used to immunize an animal (such as a rabbit, chicken, goat or sheep) by one of the known protocols that efficiently generate anti-peptide antibodies. For convenience, the peptide used for immunization and antibody purification may contain additional c-terminal residues added to the monitor peptide sequence (here abbreviated MONITOR), e.g.: nterm-MONITOR-lys-gly-ser-gly-cys-cterm (SEQ ID No. 10). The resulting extended monitor peptide can be conveniently coupled to carrier (e.g., KLH) that has been previously reacted with a heterobifunctional reagent such that multiple SH-reactive groups are attached to the carrier. In classical immunization with the peptide (now as a hapten on the carrier protein), a polyclonal antiserum will be produced containing antibodies directed to the peptide, to the carrier, and to other non-specific epitopes. Alternatively, there are many methods known in the art for coupling a peptide, with or without any extensions or modifications, to a carrier for antibody production, and any of these may be used. Likewise there are known methods for producing anti-peptide antibodies by means other than immunizing an animal with the peptide on a carrier. Any of the alternatives can be used provided that a suitable specific reversible binding agent for the monitor peptide is produced.

Specific anti-peptide antibodies (e.g., rabbit antibodies such as rabbit monoclonal antibodies) are then prepared from this antiserum by affinity purification on a column containing tightly-bound peptide. Such a column can be easily prepared by reacting an aliquot of the extended monitor peptide with a thiol-reactive solid support. Crude antiserum can be applied to this column, which is then washed and finally exposed to 10% acetic acid (or other elution buffer of low pH, high pH, or high chaotrope concentration) to specifically elute antipeptide antibodies. These antibodies are neutralized or separated from the elution buffer (to prevent denaturation), and the column is recycled to physiological conditions for application of more antiserum if needed. Antibodies also may be produced by hybridoma techniques well know in the art.

The peptide-specific antibody is finally captured or immobilized on a column, bead or other surface for use as a peptide-specific affinity capture reagent. In one embodiment, the anti-peptide antibody is immobilized on commercially available protein A-derivatized POROS chromatography media (Applied Biosystems) and covalently fixed on this support by covalent crosslinking with dimethyl pimelimidate according to the manufacturer's instructions. The resulting solid phase media can bind the monitor peptide specifically from a peptide mixture (e.g., a tryptic digest of serum or plasma) and, following a wash step, release the monitor peptide under mild elution conditions (e.g., 10% acetic acid). Restoring the column to neutral pH then regenerates the column for use again on another sample, a process that is well known in the art to be repeatable hundreds of times. In another embodiment, the anti-peptide antibodies are captured on magnetic beads (either before exposure to the digest or afterwards), which simplifies separation of antibody from the digest after peptide binding, washing, and peptide analyte recovery. High affinity (typical dissociation constants of $10^{-9}$ to $10^{-11}$), high specificity antibodies are preferred, and processes of antibody generation and selection are designed to optimize these characteristics.

Digestion of Sample to Peptides (Step d)

A protein sample such as plasma, containing the selected protein to be measured, is digested essentially to completion with an appropriate protease (e.g., trypsin) to yield peptides (including the monitor peptide selected in step 1). For a monitor peptide whose sequence appears once in the target protein sequence, this digestion generates the same number of monitor peptide molecules as there were target protein molecules in the stating sample (provided each monitor peptide sequence occurs once per protein). The digestion is carried out by first denaturing the protein sample (e.g., with urea, trifluoroethanol or guanidine HCl), reducing the disulfide bonds in the proteins (e.g., with dithiothreitol or mercaptoethanol), alkylating the cysteines (e.g., by addition of iodoacetamide), quenching excess iodoacetamide by addition of more dithiothreitol or mercaptoethanol, and finally (after removal or dilution of the denaturant) addition of the selected proteolytic enzyme (e.g. trypsin), followed by incubation to allow digestion. Following incubation, the action of trypsin is terminated, either by addition of an enzyme inhibitor (e.g., DFP, PMSF or aprotinin) or by denaturation (through heat or addition of denaturants, or both) or removal (if the trypsin is on a solid support) of the trypsin. The destruction of the trypsin activity is important in order to avoid damage to antibodies later by residual proteolytic activity in the sample.

Adding Isotopically-Labeled Monitor Peptide Internal Standards (Step e)

A measured aliquot of isotopically-labeled synthetic monitor peptide (SIS) is added to a measured aliquot of the digested sample peptide mixture in a known amount, typically close to or greater than (if the standard serve for example, as carrier for a low abundance peptide) the expected abundance of the same "natural" peptide in the sample aliquot. Following this addition the monitor peptide will be present in the sample in two forms (natural and isotopically-labeled). The concentration of the isotopically-labeled version is accurately known based on the amount added and the known aliquot volumes. The labeled peptide may be added separately from the antibody, although it can be added in combination with the antibody for stability and simplicity.

Enrichment of the Monitor Peptide by Antibody Capture and Elution (Step f)

The peptide mixture (sample digest with added isotopically-labeled monitor peptides) is exposed to the peptide-specific affinity capture reagent, which preferentially binds the monitor peptide but does not distinguish between labeled and unlabeled forms (since isotopic substitutions are not expected to affect antibody binding affinity). Following one or more wash steps (e.g., phosphate-buffered saline, water) the bound peptides are then eluted (e.g., with 5% acetic acid, or with a mixture of water, formic acid and acetonitrile), for MS analysis. The affinity support can, if desired, be recycled in preparation for another sample. In some of the high-throughput assay applications envisioned, it will be advantageous to recycle the immobilized antibodies hundreds, if not thousands, of times when flow-through columns are used. Current evidence indicates that rabbit polyclonal antibodies can be recycled at least 200 times when antigens are eluted with 5% or 10% acetic acid and total exposure to acid is kept short (e.g., less than 1 minute before regeneration with neutral pH buffer). In a capillary column format, where the immobilized antibody bed can be submicroliter in size, the duration of acid exposure could be further decreased, possibly extending the life of the immobilized antibody adsorbent even further. Magnetic bead embodiments can also be conveniently automated in a variety of ways to achieve high throughput, and avoid the potential for carryover inherent in re-usable antibody columns.

The enrichment step is an important element of the method because it allows enrichment and concentration of low abundance peptides, derived from low abundance proteins in the sample. Ideally, this enrichment process delivers only the monitor peptide to the MS, and makes its detection a matter of absolute MS sensitivity, rather than a matter of detecting the monitor peptide against a background of many other, potentially much higher abundance peptides present in the whole sample digest. This approach effectively extends the detection sensitivity and dynamic range of the MS detector in the presence of other high abundance proteins and peptides in the sample and its digest.

Analysis of the Captured Monitor Peptides by Ms (Step g).

The monitor peptide (including natural and isotopically-labeled versions) enriched in the preceding step is delivered into the inlet of a mass spectrometer (e.g., by MALDI or by electrospray ionization (ESI)). The mass spectrometer can be a TOF (time-of-flight), a Q-TOF, a TOF/TOF, a triple quadrupole, an ion trap, an orbitrap, an ion-cyclotron resonance machine, or any other instrument of suitable mass resolution (>1,000) and sensitivity, and can employ one, two, or more levels of mass selection interspersed with analyte fragmentation processes (e.g., collision-induced fragmentation).

The MS measures the ion current or ion count (number of ions) for both versions of the monitor peptide (natural and labeled), typically as a function of time or within an accumulated spectrum (in the case of TOF-MS). The ion current may be integrated over time (ideally for as long as the monitor peptide appears in the mass spectrum) for each mass species, and the integrated amounts of natural and isotope-labeled forms are computed as measures of peptide amount. Alternatively the maximum peak heights of the natural and labeled peptides can be used as measures of peptide amount.

Computation of Abundance of Each Monitor Peptide in the Sample (Step h)

A ratio is computed between the amounts of the labeled and unlabeled (natural) monitor peptides. Since the amount of labeled peptide added is known, the amount of the natural monitor peptide derived from the sample digest can then be calculated by multiplying the known concentration of labeled monitor peptide by this measured ratio. By assuming that the amount of the monitor peptide in the digest is the same as (or closely related to) the amount of the parent protein from which it is derived, a measure of the protein amount in the sample can be obtained.

The foregoing description outlines the SISCAPA method, which while one embodiment of the application of the present technology, is not the only application envisioned.

2 Determination of Clinical Cutoff and Clinical Reference Interval.

For quantitative tests in which deviation from 'normal' in one direction is significant (e.g., a level of a cancer marker like PSA or CA125 above a cutoff value) but where deviation in the other direction (usually lower than 'normal') is not considered significant, only one threshold—the test "cutoff"—is needed. For tests in which a deviation from a normal range in either direction can be significant, test values are typically interpreted against the upper and the lower bounds of the established reference range. Physicians frequently use this method of interpretation to identify significant test results that are likely to bear on a patient's diagnosis or treatment. Cutoffs and reference range boundaries are typically established by making analyte measurements in a large group of patients, developing the histogram of these values and selecting points for which only a small fraction (usually ~2.5%) of the 'normal' population give results outside the points. Cutoffs or reference intervals can be established as part of FDA approval processes, and may be superseded by reference range studies within a clinical institution to better reflect the normal population of patients in that institution, or even by personal reference values used in interpreting individual patient test results over time.

3 Internal Standard Peptides and Proteins, and Isotopic Labeling Schemes.

SIS peptides can be synthesized containing a variety of combinations of labeled amino acids. Thus, different versions of the same SIS peptide can be made that, while chemically identical to the analyte peptide, are nevertheless distinguishable from the analyte and from each other by mass. Such different peptides can be used together in an assay to provide two or more internal standards spiked into the sample or its digest at different levels.

4 Providing Internal Standards at Clinical Cutoff and Reference Levels.

The level(s) of one or more internal standards can be selected to equal or approximate clinically important analyte concentrations. Using standards present at clinical decision levels has major advantages in an analytical procedure. First, it is it possible to confirm the result of the test by inspection of raw MS data: in almost all cases it is clear whether the analyte peptide produces a signal that is greater than or less than that of the analogous internal standard. This is true whether peak height or a peak area is compared. Secondly, the precision of comparing the amount of an analyte to an internal standard is typically highest when the two are present at near equal amounts in a standardized sample: this minimizes the effect of any non-linearity in the response of the MS detector (which may become significant when analyte and standard are present in different amounts), and eliminates any uncertainty as to the true position of the decision value in relation to the internal standard. Thirdly, when analyte and standard are present at near-equal amounts, the signal-to-noise and statistical precision of the two measurements are likely to be very similar, thereby simplifying the quality control of an assay. Thus, if the assay yields a measurement for an internal standard that is large enough to ensure adequate precision (e.g., in comparison with prior quality studies relating magnitude of such measurements with replicate precision) then a single measurement of analyte in a sample yielding a similar amount is likely to have similarly adequate precision. Finally, "hard-wiring" a decision threshold into an assay kit, for example by depositing an amount of SIS in or on a single-use component of an assay kit such that the provided amount of SIS dissolves in an accurately measured amount of sample, provides a major advance in the reliability of the overall assay result.

5 Comparison of Analyte Levels to Internal Standards: MALDI and ESI.

Figure 2:
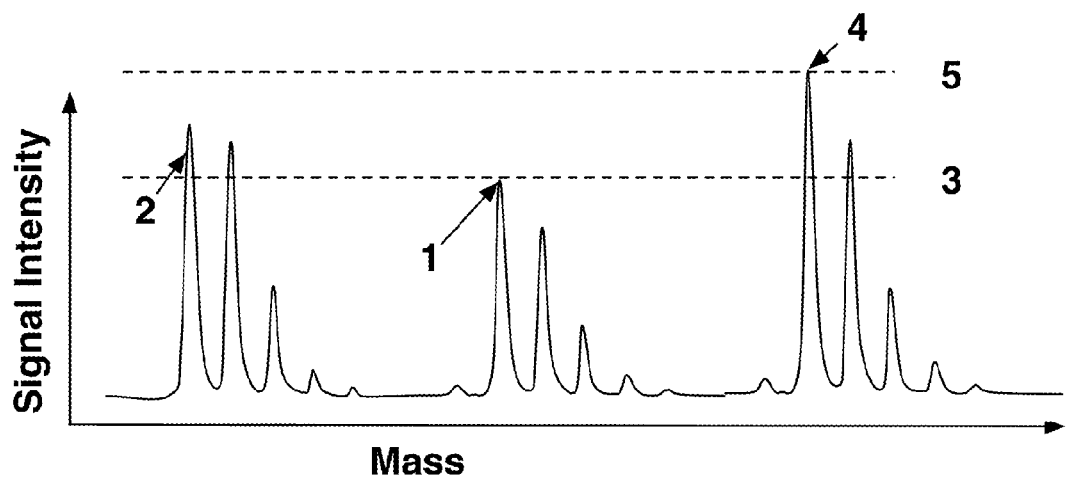
FIG. 2. Comparison of analyte and two internal standard peptides by MALDI-MS. One internal standard 1 is present at a concentration equal to the lower limit of the analyte reference interval 3, and the other 4 is present at the upper limit of the interval 5.
Figure 3:
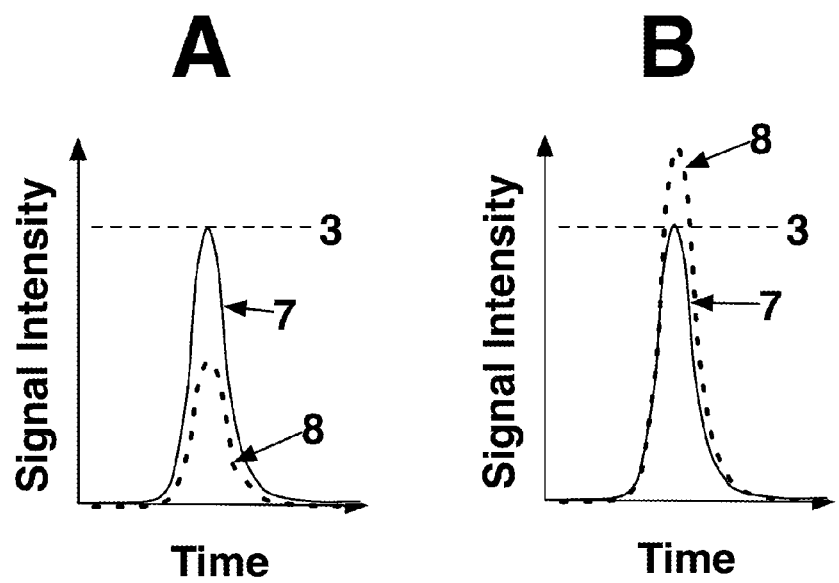
FIG. 3. Comparisons of analyte and internal standard amounts by selected reaction monitoring LC-MS/MS.
Figure 4:
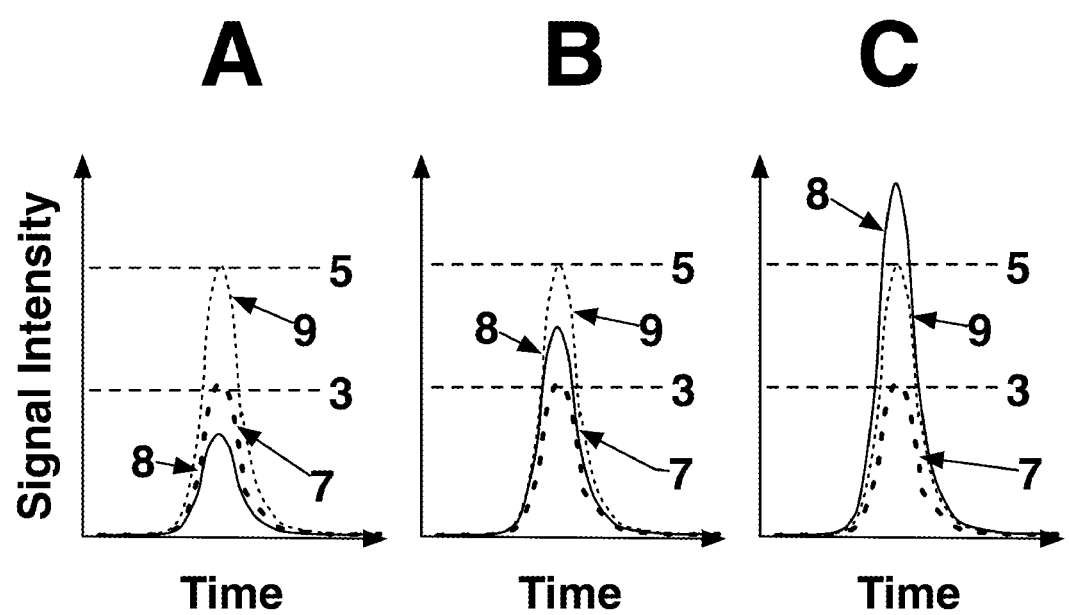
FIG. 4. Comparison of analyte and two internal standard peptides by selected reaction monitoring LC-MS/MS.

The present technology provides an improved method for assessing analyte concentration in the sample against the appropriate clinical criteria (either a cutoff or a reference range). The principal is illustrated for the case of MALDI-TOF mass spectrometry in FIG. 1A, where the peak height for the major isotopic form of internal standard 1 establishes the cutoff level 3 equal to the assay cutoff: the concentration of the standard is set deliberately to equal this clinically determined cutoff. The measured height of analyte peak 2 is compared to cutoff 3 and easily judged to be less than the cutoff, thus providing the result of the binary test. In FIG. 1B, the alternative situation is shown, in which the analyte peak 2 is taller than the cutoff 3 set by the internal standard 2, indicating that the analyte concentration exceeds the clinical threshold. It is equally possible, though less intuitive and direct, to use alternative measures such as peak area in place of peak height. The advantage of peak height in this context is that the result can be 'read' directly from the primary MS output—a plot of signal intensity versus either mass (or m/z) in TOF-MS, or versus time in liquid chromatography mass spectrometry methods (LC-MS). The mass accuracy of modern TOF mass analyzers is sufficient (1-20 ppm) to provide strong evidence of the identity of the expected analyte and SIS peptides. FIG. 2 illustrates the comparison of the analyte (peak 2) with SIS internal standard 1, which establishes the low end 3 of the reference interval, and with a different SIS internal standard 4, which establishes the upper end 5 of the reference interval. It is immediately evident that the analyte concentration lies within the reference interval. FIG. 3 shows the equivalent situations measured by selected reaction monitoring LC-MS/MS, carried out using a triple quadrupole MS. In this case sample peptides are separated over time by reversed-phase liquid chromatography, but, being chemically identical, the analyte and SIS internal standards elute simultaneously. In FIG. 3A, analyte peak 8 has both less height and lower peak area than internal standard peak 7 indicating a test result of less than the cutoff 3; in FIG. 3B, the alternative situation (analyte amount greater than the cutoff) is shown. FIG. 4 shows the LC-MS cases in which analyte peak 8 is below the reference interval lower bound 3 (FIG. 4A); between reference interval boundaries 3 and 5 (FIG. 4B); or above the reference interval upper bound 5 (FIG. 4C). As in the case for MALDI peaks, the result of the test is immediately evident through comparison of the analyte peak with internal standards set at the clinical cutoff or reference interval upper and lower bounds. When desirable, as for example in the context of personalized medicine, the cutoff or reference interval can be set based on a patient's past analytical history (the past values of tests for the same analyte). This approach takes into account the differences between individuals by using the individual as his or her own control. It is more difficult technically to provide individually personalized internal standard concentrations in routine assays, but this can be done using a database of personal test values and accurate technology for spiking variable levels of standards in each sample analyzed. Thus, in one embodiment the amount of internal standard utilized will be an amount based upon past measurements of an individual patient (subject).

When peak heights and peak areas are obtained within a spectrum of sufficient resolution so as to effectively resolve isotopic peaks, such as when conducting comparisons of peak heights and peak areas obtained within a spectrum (e.g., using MALDI-TOF mass spectrometry), one or more specific isotopic composition peaks from the natural and labeled forms can be selected for comparison. With such resolved isotopic peaks it is facile to compare peak heights directly in a raw or smoothed spectrum, and this provides a preferred means of determining the relationship between an analyte and a corresponding SIS present at a test evaluation threshold so as to deliver a test result. Peak areas can be similarly compared after computation by summing measurements within the peak (e.g., by numerical integration) or by fitting an empirical or modeled peak shape to the spectral data to obtain the peak area.

When peaks occur in a time domain (e.g., MRM peaks observed during the course of a chromatographic separation of peptides), such as when conducting comparisons of peak heights and peak areas using LC-MS/MS, additional instrument factors may come into play. In a triple quadrupole mass spectrometer, resolution is typically not sufficient to deliver baseline separation between isotopic forms, and the mass-domain envelope determining what is detected may not be a rectangular step function, but another peak distribution, the width of which can be altered by instrument settings (e.g., the "resolution" setting common on triple quadrupoles). Because of these features, the height or area obtained for a specific isotopic peak may vary slightly depending on the relative abundances of adjacent isotopic forms of a peptide, varying amounts of which may be enclosed within the detected envelope along with the target isotopic form. These relative abundances often differ between labeled and unlabeled peptides, in large part because of the use of heavy label isotopes with less than perfect levels of enrichment ($^{13}$C and $^{15}$N are often available at 98% isotopic substitution, but not 100%), resulting in different relative abundances of peaks adjacent to the labeled vs unlabeled peaks to be measured. Since different specific instrument designs and tuning parameters may therefore alter slightly the observed ratios between analyte and SIS peaks, it may be necessary to apply a correction factor to the measured ratio to obtain an accurate comparison between the two. Such a factor can be determined accurately and precisely from calibration experiments using synthetic peptides. When the present invention makes use of peak height and/or area comparisons, the use of such correction factors is optionally incorporated in the data processing method used.

6 Precision and Accuracy of MS Measurements.

Given the fact that MS measurements are not infinitely precise, occasions will arise in which a test analyte occurs at a level very close to the SIS internal standard level. In the event that the analyte level occurs within a defined interval around the SIS level, for example a statistically defined interval such as +/−3, 2, 1, ½ or ¼ standard deviations determined from the SIS measurement, then it may be advantageous to report a 'grey area" or indeterminate result. An advantage of the present approach is that such a grey area interval can be extremely narrow, and hence occur in an extremely small subset of samples.

7 Multiplex Tests Measuring Multiple Analytes.

Multiplex tests measuring multiple analytes can be evaluated by comparison with multiplex SIS peptides present at pre-determined test evaluation thresholds. In the simplest case, the amount (e.g., peak height) of each analyte is compared to the amount of the corresponding SIS (present at an analyte-specific decision level) to obtain a binary ("High" or "Low") result. These binary results are then evaluated against a matrix of possibilities (in principle all possible result patterns), each of which is associated uniquely with an overall test result, and the result corresponding to the matching pattern is delivered as the result.

8 Packaging Peptides on a Carrier to Avoid Loss.

Providing SIS peptides in assays at concentrations accurately representing clinical decision, or other, values or ranges requires accurate and precise control of peptide delivery, and consequent minimization of peptide loss or deterioration prior to use. Synthetic peptides of the size and composition of typical tryptic (or other cleavage agent-produced) peptides exhibit a wide range of physical properties, particularly as regards solubility, and conversely, stickiness to polymer, glass, and other surfaces found in storage containers, laboratory ware, pipettes, LC tubing and the like. Peptides with sticky character, often associated with high hydrophobicity, frequently exhibit poor recovery from storage containers or during handling processes. Recovery is typically worst for peptides at low abundance (when the ratio between surface adsorptive sites and peptide is high), and it is well known that recovery of femtomole amounts of peptides from typical polypropylene storage tubes can be very poor. In one embodiment, the technology described herein formulates peptides in such a way that such losses are minimized, thus providing improved recovery of peptides for use, e.g., as internal standards in mass spectrometric assays such as the SISCAPA method. One approach described here to improve recovery is to link peptides to a larger carrier molecule or particle having good storage and recovery properties, e.g., a large hydrophilic, soluble protein or else a visible particulate bead (e.g., a magnetic bead). In suitably designed carriers, the bulk properties of the carrier override the problematical properties of the peptide(s), giving the combined object the desired high recovery from storage.

9 Linkage Between a Peptide and a Carrier.

A variety of linkage interactions are possible for coupling peptides to a carrier, including covalent reactions between sulfhydryls (e.g., cysteine) and maleimides, "Solulink chemistry" (reaction of 6-hydrazino-nicotinamide (HyNic) with carbonyl moieties), etc., or non-covalent but tight interactions such as those between biotin and avidin (or streptavidin), and between a hexahistidine tag and immobilized nickel. In one embodiment, the peptide linkage site consists of a cysteine sulfhydryl, the C residue comprising a part of the extension sequence of an extended SIS peptide, and the carrier linkage site consists of a maleimide group covalently attached to a protein carrier such as KLH. Alternatively, a peptide may be provided bound non-covalently to a surface that contacts the sample or digest at some point in the analytical workflow, such that the peptide is released by dissolution upon such contact. In other embodiments, the polySIS peptides are immobilized on a carrier using any of the above-described linking interactions.

10 Recovery of Peptides from a Carrier by Proteolytic Cleavage.

For many of the applications for synthetic peptides described here, particularly use as internal standards in analytical mass spectrometry, the SIS peptide material must ultimately be delivered as a molecule of the correct length (i.e., the same length and structure as the analyte for which it serves as an internal standard) free in solution at a known concentration. Thus, it is desirable for all (or at least some known fraction) of the peptide(s) packaged on a carrier to be released and made available as an internal standard for direct MS quantitation of the corresponding sample-derived target peptide or else for treatment by some selection, fractionation or specific capture method that enriches the analyte peptide and the SIS together, preserving their ratio to provide analyte concentration upon MS analysis. Proteolytic cleavage of a sample into peptides is a common feature of sample preparation for analysis of protein samples by MS, including those involving a specific enrichment step (e.g., the SISCAPA method). It is possible and efficient therefore to use the same proteolytic process to liberate peptides from a carrier, and in the simplest case to accomplish this at the same time as sample digestion by adding the peptide-carrier conjugate to the sample before digestion, thereafter digesting both sample and conjugate together. In particular when the peptide linkage site connecting the peptide to the carrier is present in the extension portion of the extended peptide (i.e., the portion not within the SIS peptide) then proteolytic cleavage of the bond between the SIS and the extension will release intact SIS from the carrier (with the peptide linkage site and the extension remaining on the carrier). In the case where the proteolytic cleavage is carried out by the enzyme trypsin, then the junction between SIS sequence and the extension is a tryptic cleavage site (i.e., a K or R residue followed by any amino acid except P). If the extension portion of the peptide is n-terminal to the SIS sequence, then the extension will consist of an arbitrary sequence of amino acids ending in K or R, and the tryptic cleavage will occur after this K or R, releasing the c-terminal SIS sequence. If the extension is c-terminal to the SIS sequence, then, since the SIS (having the same sequence as a tryptic peptide) will end in K or R the SIS sequence will be cleaved by trypsin from the c-terminal extension sequence, provided that the extension sequence does not begin with a proline. Extension sequences can contain additional amino acid residues to space the cleavage site away from the carrier, reducing steric hindrance to the action of the cleavage enzyme. Extension sequences can be generic (such as GSG or GSGSG sequences (SEQ ID Nos. 1 and 2, respectively) or they can comprise flanking sequence from the target protein sequence (i.e., an n-terminal extension could consist of a stretch of amino acid sequence immediately n-terminal to the analyte peptide sequence). The latter approach provides a cleavage site sequence environment most closely approximating that in the sample protein target, and therefore may help to normalize SIS release to parallel release of analyte peptide during sample digestion.

11 Surrogate Quantitation of SIS Peptides by Measuring the Amount of Carrier.

An easily quantitated or identified physical or chemical property of the carrier can allow facile detection and measurement of its amount. Suitable properties include optical absorbance (e.g., for naturally colored protein molecules such as the heme-binding domain of cytochrome b5), fluorescence (e.g., found in the green fluorescent protein and its derivatives), content of biotin groups (which can be assayed competitively or directly using well-known biotin binding proteins such as avidin or streptavidin), magnetic properties (e.g., measurable in magnetic beads or the protein ferritin), weight (e.g., dry mass), or even countability (e.g., for 2-50 micron diameter bead materials which can be counted directly in a flow cytometer). In some cases two properties can be used together to establish an improved quantitation method, such as when particles carrying a fluorescent chromophore are measured in a flow cytometer that is capable of both quantitating fluorescence of each particle and counting the particles. Using these or similar properties, the amount of carrier can be directly determined at any time, from manufacture until use in an assay. Provided that a quantitative determination is made of the amount (e.g., moles) of peptide bound by a measurable amount of the carrier, then the amount of peptide being added as carrier conjugate can be determined indirectly by quantitation of the carrier at any subsequent time. This approach makes it possible to know and specify the amount of added carrier and attached SIS peptide at the time of addition to the sample (before or after digestion), and can be used both to verify addition of the desired amount of SIS internal standard, and to control addition to ensure the correct amount is added (e.g., when the added carrierSIS material passes a quantitative sensor that provides feedback to a valve such that the valve opens to allow a predetermined measured quantity of the carrierSIS to pass by, after which the valve shuts.)

12 Use of a Magnetically Manipulatable Carrier.

A carrier consisting of magnetic beads is particularly favorable due to the ease with which it can be transported into reactions with minimal added fluid volume (thus avoiding dilution), and the ease with which the carrier can be removed from a sample following the release of peptide (e.g., by proteolytic cleavage). Such beads are available in a range of sizes from 200 microns to 20 microns to 1 micron to less than 100 nm diameter, and with a variety of surface coatings. Extended SIS peptides having an n-terminal CGSG-extension (SEQ ID No. 3) can be coupled to beads that have been previously coated with a protein activated with 4-(N-Maleimidomethyl)cyclohexane-1-carboxylic acid 3-sulfo-N-hydroxysuccinimide ester (a heterobifunctional crosslinking reagent that reacts with protein primary amino groups to provide sulfhydryl-reactive maleimide groups on the protein surface). Immobilization of the protein on a magnetic bead surface facilitates carrying out this stepwise treatment, in which beads can easily be moved from reagent to reagent, as well as final washing of the bead-SIS peptide conjugate to remove any weakly or non-specifically bound peptide. Numerous alternative methods of linking peptides to beads of various forms are known to those skilled in the art.

13 Packaging Collections of Peptides at Defined Stoichiometry on Carriers.

Two or more different peptides, comprising two or more different SIS peptide sequences, can be linked to the same carrier preparation in a known stoichiometric relationship (e.g., one peptide present at 3.5-fold greater molar amount than a second peptide) yielding a stable mixture whose molar ratio is protected against perturbation by preferential loss of one component.

14 Providing Concentration Curves Via Sis on Carriers.

Two or more different SIS versions of a single analyte peptide sequence, each differing from the analyte and each other only in mass, can also be linked to a carrier in established molar ratios. Such a construct provides a series of distinguishable peptide internal standards at different known amounts, thus establishing the basis of an internal calibration curve when measured quantitatively by mass spectrometry.

15 Providing Mixtures of Carriers.

Two or more carriers prepared according to these concepts can be mixed in defined ratios to prepare more complex internal standards.

Embodiments

1) In a first embodiment, an internal standard stable-isotope labeled peptide is added to the sample digest prior to antibody enrichment in a SISCAPA assay at a concentration equal to the established test evaluation threshold of the assay. After elution of the captured peptides from the SISCAPA capture agent, the peptides are analyzed by mass spectrometry. The result of the test is read by comparing the height (or area) of the predominant analyte peak with the height (or area) of the predominant internal standard peak, or more generally by comparing the height (or area) of one or more pre-specified analyte peaks with the height (or area) one or more pre-specified internal standard peaks.

2) In another embodiment, first and second internal standard stable-isotope labeled peptides (identical in chemical structure to each other and to the analyte, but differing in mass) are added to the sample digest prior to antibody enrichment in a SISCAPA assay at concentrations equal to i) the established clinical reference interval lower limit, and ii) the established clinical reference upper limit, respectively. After elution of the captured peptides from the SISCAPA capture agent, the peptides are analyzed by mass spectrometry (e.g., MALDI mass spectrometry). The result of the test is read directly by comparison of the height of the predominant analyte peak with the height of the predominant peaks of each internal standard to determine if the analyte is below, within, or above the reference interval (as illustrated in FIG. 2).

3) In another embodiment, the assay of the previous embodiment is carried out, but analyzed using selected reaction monitoring MS on a triple quadrupole instrument. The result of the test is read directly by comparison of the peak area of the predominant analyte peak with the peak areas of the predominant peaks of each internal standard to determine if the analyte is below, within, or above the reference interval (as illustrated in FIG. 4).

4) In another embodiment, first and second internal standard stable-isotope labeled peptides (identical in chemical structure to each other and to the analyte, but differing in mass) are added to the sample digest prior to antibody enrichment in a SISCAPA assay at concentrations (relative to the sample) equal to i) a calculated personal reference interval lower limit, and ii) a calculated personal reference upper limit, respectively. The personal reference interval is computed based on previous analyses of samples from the same individual, and thus represents a personalized reference interval. The addition of SIS peptides is carried out by a computer-controlled dispenser that determines patient identity from the identifying code of the present sample, uses it to search for previous result values or personal reference values in a database, recovers or computes the most current and appropriate updated personal reference values, and delivers into the sample amounts of the first and second internal standard peptides equivalent to the calculated lower and upper limits in relation to the amount of patient sample contained in the present analysis. After elution of the captured peptides from the SISCAPA capture agent, the peptides are analyzed by mass spectrometry to determine if the analyte level is below, within, or above the reference interval. In all of the above embodiments, quantitative analyte concentrations can be calculated, as in the original SISCAPA method, from the ratio of analyte peak height or area to SIS peak height or area, reported with the direct comparison test result, and can be stored in a database to enable subsequent use as a basis of comparison for future test results.

5) In another embodiment, a series of individual analytes is measured in a multiplex assay, and each analyte is compared against its respective SIS internal standard which has been added to the sample at its respective predetermined multiplex test threshold. Evaluation of the multiplex test result consists by determining a result for each individual analyte and then evaluating the panel of analyte results together by lookup in a predetermined outcome table as shown below. The table contains multiplex test results for each possible set of individual analyte results. A specific test result set, shown on the right, is compared with the table to look up the multiplex result, in this case positive.

6) In another embodiment, a known molar amount of an extended SIS peptide (corresponding to a selected analyte peptide of a target sample protein) is reacted with a molar excess of maleimide groups on activated KLH carrier protein to form a carrierSIS conjugate. A known amount of this conjugate (carrying a known molar amount of extended SIS peptide) is added to a known volume of protein sample such as human plasma, and the combined spiked sample digested with trypsin to yield tryptic peptides. The analyte peptide (produced by tryptic cleavage of the target protein) and the corresponding SIS peptide (produced by cleavage between the SIS sequence and the extension linking it to the carrier) are analyzed by quantitative mass spectrometry to provide a ratio of analyte:SIS. Multiplying this ratio by the known molar quantity of SIS added as part of the conjugate yields the molar amount of the analyte peptide, and thus provides a measure of the amount of the target protein in the sample.

7) In another embodiment, a green fluorescent protein (GFP) is used as carrier instead of KLH in the process described in the embodiment above. The resulting carrierSIS preparation containing a known molar amount of each extended SIS peptide is characterized by fluorescence spectrophotometry to determine the amount of fluorescence emission per nanomole of SIS peptide. The amount of carrierSIS to be added is confirmed either before or after addition to the sample by fluorescence emission by GFP. Because GFP is extremely resistant to tryptic cleavage, the amount of carrier can also be measured during or after digestion.

8) In another embodiment, multiple carrierSIS products are made in order to facilitate standardized measurement of proteins having widely different abundances in the sample. Thus, a first carrierSIS product includes SIS peptide sequences corresponding to tryptic peptides from proteins having expected concentrations around 1 mg/ml in human plasma (e.g., hemopexin and alpha-1-antichymotrypsin, while a second carrierSIS product is made containing monitor peptide sequences from low abundance (e.g., 10-1000 pg/ml) proteins such as IL-6 and TNF-alpha. Since the mass spectrometer detection systems used to measure the relative abundances of natural and SIS peptides have limited dynamic range (typically 100 to 10,000), it is desirable to add an amount of each SIS peptide close to the expected amount of the equivalent natural monitor peptide. Thus, the second carrierSIS described would optimally be added at a level approximately 1,000,000-fold less than the first carrierSIS above. In cases where the numbers of SIS peptides required in quantitative studies exceed the number that can conveniently be prepared as one carrierSIS protein, it is natural and efficient to group the desired SIS peptides into classes according to the expected concentration of the proteins from which they arise in the sample. If a set of monitor peptides were selected within a decade of concentration range (i.e., all members

| | | | | | | | Analyte Evalution table | | | | | | | | | | Result compared to SIS |
|---|---|---|---|---|---|---|---|---|---|---|---|---|---|---|---|---|---|
| 1 | Hi | Lo | Hi | Lo | Hi | Lo | Hi | Lo | Hi | Lo | Hi | Lo | Hi | Lo | Hi | Lo | Hi |
| 2 | Hi | Hi | Lo | Lo | Hi | Hi | Lo | Lo | Hi | Hi | Lo | Lo | Hi | Hi | Lo | Lo | Lo |
| 3 | Hi | Hi | Hi | Hi | Lo | Lo | Lo | Lo | Hi | Hi | Hi | Hi | Lo | Lo | Lo | Lo | Lo |
| 4 | Hi | Hi | Hi | Hi | Hi | Hi | Hi | Hi | Lo | Lo | Lo | Lo | Lo | Lo | Lo | Lo | Hi |
| Result | Pos | Pos | Pos | Pos | Neg | Pos | Pos | Neg | Neg | Neg | Neg | Neg | Pos | Neg | Neg | Neg | | within a factor of 10 in expected concentration), then 6 carrierSIS products would be required to span a total dynamic range of 1,000,000 between the most and least abundant target protein. It is also possible to employ carrier polySIS peptide complexes where the polySIS peptides contain different SISpeptide subsequences in different relative proportions to facilitate standardized measurement of proteins at different abundances (e.g. the subsequences may be preset at a ratio selected from: 1:20, 1:10, 1:8, 1:6, 1:4, or 1:2).

9) In another embodiment, magnetic particles coated with maleimide-activated protein are used as carrier. In this case an excess of particles (in terms of moles of reactive maleimide) is reacted with a known molar amount of extended SIS peptide having an n-terminal Cys in the extension. A known fraction of the resulting preparation in liquid suspension is added to a protein-containing sample and digested with trypsin. After digestion, a magnet is used to remove the carrier particles. The SIS-spiked sample, without the carrier, is analyzed by mass spectrometry.

10) In another embodiment, unequal stoichiometries between two or more individual SIS peptides are achieved by coupling a mixture of extended SIS peptides, wherein each is present at a known molar concentration, with an excess of activated carrier. Thus, a carrierSIS product with 1 copy of a SIS sequence denoted A, 2 copies of a SIS sequence denoted B, 4 copies of a SIS sequence denoted C and 10 copies of a SIS sequence denoted D can provide peptide standards at concentrations that match the amounts of monitor peptides derived from proteins expected to be present at relative concentrations of 1:2:4:10 in the original sample. Alternatively, a carrier bearing a polySIS (carrierPolySIS) sequence in which the subsequences A, B, C and D were present in a ratio of 1:2:4:10 respectively could achieve essentially the same result and would require fewer binding sites on the carrier to incorporate the same molar amount of total SIS peptides that would be released into the sample.

11) In another embodiment, two or more monitor peptide sequences are selected from the digest products of a single target analyte protein, and extended SIS sequences for each of these are incorporated into the carrierSIS product. Thus, SIS sequences A, B and C from a given target protein may be incorporated into the carrierSIS at equal molar amounts, or alternatively different molar amounts (e.g., at the upper and lower concentrations of a normal range for an analyte protein). Measurement of multiple monitor peptides from a single protein target (in which the peptides are present at defined, usually 1:1:1, stoichiometry) and comparison to multiple SIS peptides added at accurately defined 1:1:1 stoichiometry in a carrierSIS mixture provides improved measurement precision and allows accurate detection of situations in which only part of a target protein is present. Alternatively, addition of a polySIS peptide or carrierPolySIS conjugate in which the subsequences A, B, and C are present in a ratio of 1:1:1 respectively could achieve the same increase in precision, and would require calibration of only one internal reference standard.

12) In another embodiment, an easily assayed substituent is incorporated into the carrierSIS and used for later quantitation of the carrierSIS conjugate. An example is the incorporation of biotin groups. The presence of the biotin group at 1 mole per mole of carrierSIS allows absolute quantitation of the carrierSIS through use of a standard assay for the biotin tag (e.g., a competition assay using immobilized streptavidin as capture agent and a biotinylated acid phosphatase with the competing ligand able to generate a colorimetric signal). In addition, the biotin tag can be used for purification of the bulk carrierSIS conjugate (where this is of molecular dimensions) by binding to a streptavidin column. The carrierSIS can be released from such a column by selective elution or by cleavage at a peptide sequence linking the SIS sequences to the biotinylated site using a specific protease (e.g., Factor Xa) with a specificity different from the protease used to liberate SIS (e.g., trypsin).

13) In another embodiment, entire domains of target proteins that are labeled with stable isotopes (e.g., during in vitro or in vivo expression or chemical synthesis) are coupled to the carrier instead of short individual extended SIS peptide sequences. In this approach, each domain contains at least one SIS peptide (e.g., tryptic SIS peptide(s)). In those embodiments where one or more domains contain several peptides suitable for measurement by mass spectrometry (e.g., tryptic SIS peptides), those domains offer multiple opportunities to quantitate the target. More importantly, by including entire domains likely to fold in a manner more similar to the fold of part of the intact whole target protein, the carrierSIS better replicates the environment within which the proteolysis will occur for the native target protein—i.e., the cleavage of the peptides in the carrierSIS may better parallel the efficiency in the target.

14) In another embodiment, one or more SIS peptides are applied in known amounts to a surface of a single-use component provided in an assay kit, in a form that preserves peptide integrity during kit storage and allows release of the SIS when the surface contacts the sample. For example, three SIS peptides are deposited at the bottom of a well of a polypropylene 96-well plate in a small volume of an aqueous matrix containing dissolved trehalose and then dried in place, each in an amount equal to that required to establish a respective pre-determined test evaluation threshold in a specified volume (e.g., 100 microliters) of a protein-containing sample such as human plasma or a digest of plasma. Once the pre-specified volume of applied sample dissolves the dried SIS peptides, they are available to act as internal standards. A variety of peptide stabilizers are known in the art that are capable of incorporating or adsorbing SIS peptides in such a way that they readily dissolve in an applied liquid sample. Such surface applied SIS peptides can be placed in or on tubes, microtiter wells, pipette tips, pins, and other single-use components of an assay kit to provide accurate amounts of internal standard. Use of this approach has the advantage that the amount of SIS delivered per assay is controlled at the point of manufacture of the component and does not depend on the accuracy of SIS dispensing at the point of use. CarrierSIS conjugates, polySIS polypeptides, or carrierPolySIS conjugates can be similarly placed on surfaces in place of SIS peptides. Components that are exposed to the digestion process (e.g., to a proteolytic enzyme) are appropriate sites for covalent binding of carrierSIS to which SIS are linked by a proteolytically cleavable linker.

EXAMPLES

In a first example, a tryptic peptide analyte (having sequence FSPDDSAGASALLR (SEQ ID No. 4) and protonated monoisotopic mass 1406.691) is selected to allow measurement of human thyroglobulin in plasma. Synthetic peptides having this sequence are generated by conventional solid phase peptide synthesis using i) precursors with natural isotopic composition (i.e. yielding an unlabeled peptide equivalent to the analyte) and ii) the same precursors except for use of labeled arginine (whose precursor is substituted with $^{13}C$ and $^{15}N$ at all positions), yielding a SIS peptide with a stable isotope labeled c-terminal arginine residue and hence a mass that is 10 atomic mass units (amu) greater than the unlabeled analyte.

A series of dilutions of synthetic analyte peptide are prepared, each containing the same concentration of the SIS version of this analyte, so that the ratio of analyte to SIS amounts varies across the dilution series. In this example, the amount of the SIS version illustrates the clinical decision point of an assay for the peptide. Thus, in the simplest embodiment described here, the result of the assay is given by comparing the amount of the analyte to the amount of the SIS and providing a binary assay result depending upon whether the analyte is present in greater or lesser amount than the added SIS here used as an internal standard at a clinical decision threshold. Two ul (microliters) of peptide samples were applied to MALDI matrix spots on a pre-spotted MALDI target (Eppendorf Pre-spotted Anchor Chip targets sold by Bruker Daltonics) in 5% acetic acid for 3 minutes, followed by 5 ul of ammonium phosphate in 0.1% trifluoroacetic acid, after which the liquid was withdrawn and the target dried in air. MALDI spectra were obtained with a Bruker Autoflex MALDI mass spectrometer in reflection mode, and processed using Bruker flexAnalysis software to yield centroid peak heights and areas.

Figure 5:
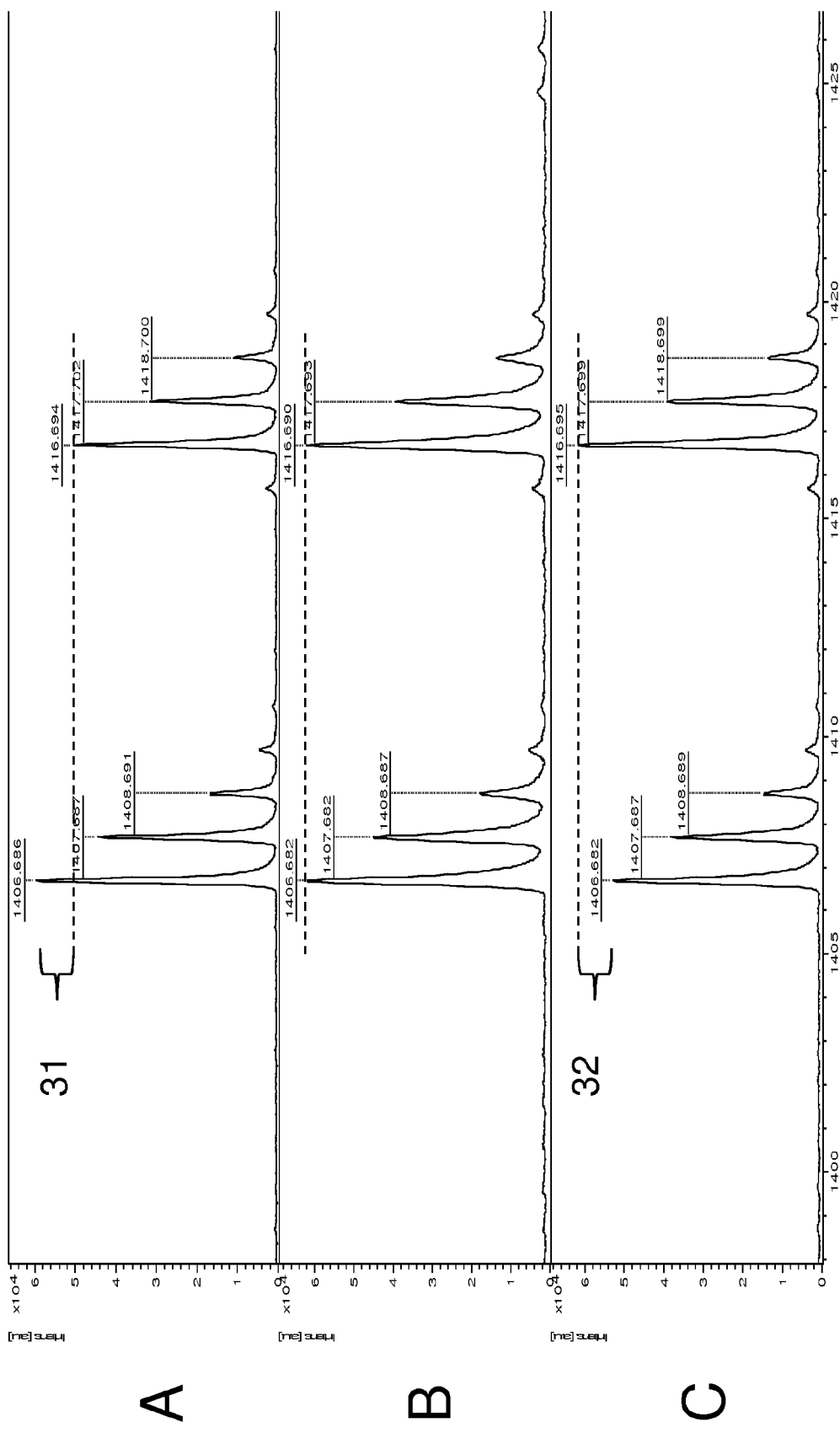
FIG. 5. MALDI comparisons of analyte and SIS peptide levels.

FIG. 5 shows the MALDI mass spectra of three samples in the dilution curve: A in which the unlabeled analyte peptide (at mass 1406.7) is present in an amount greater than the SIS at mass 1416.7, the difference in peak heights being amount 31; B in which the amounts are very nearly equal; and C in which the analyte peak is less than the SIS peak by amount 32. The ratios of the heights (intensities) of the major analyte to SIS peaks in A, B and C are 1.183, 0.991, and 0.856, with coefficients of variation of 2.1%, 1.1% and 1.8% across a series of replicate MALDI spots (4, 3, and 4 spots respectively). Panel A thus represents a case in which the analyte is about 19% greater in intensity than the SIS, which given an average CV (coefficient of variation=standard deviation divided by the mean) in this range of 1.7%, is almost 12 standard deviations above the clinical decision level. Panel C represents a case in which the analyte is about 14% below the intensity of the SIS, which is more than 8 standard deviations below the clinical decision level. If centroid peak area is used instead of peak intensity, the respective ratios are 1.187, 1.003, 0.837. Clearly the detection scheme illustrated here can unequivocally determine that analyte is more or less than the clinical decision level by ~15% with extreme statistical precision (i.e., more than 8 standard deviations).

Panel B of FIG. 5 represents a case in which the analyte level is very close to the clinical decision level (assumed here to be the known level at which the SIS peptide is added to the sample). A set of 4 MALDI target spots prepared from each of 3 replicate dilution series (12 total replicates) of the composition shown in panel B were analyzed by MALDI and the results for the analyte and SIS peaks obtained. The average ratio over 12 replicates between analyte and SIS peak heights (intensities) was 0.9998 with a CV of 1.5%. The average ratio over 12 replicates between analyte and SIS peak areas (calculated by a centroid algorithm) was 0.9948 with a CV of 1.1%. Any ratio that is more than 4.5% above or below a measured ratio of 1.0 would therefore represent a significance of 3 or more standard deviations from the clinical decision level. This level of result precision in relation to a clinical decision level is better than most current clinical protein immunoassays, both in terms of absolute precision of measurement and because of the ability to use internal, rather than external, standardization (contributing to better test accuracy).

In a second example, a series of peptide analytes at approximately equal molar abundances is used to prepare a series of dilutions in relation to fixed concentrations of the SIS versions of the same peptides, illustrating in one embodiment the method applied to a multiplexed test situation. Analyte peptides 1-5 are measured (as peak intensity) in relation to SIS peptides 1-5 added as internal standards at their respective multiplex test thresholds. Analytes 1 and 4 exceed their respective thresholds, while analytes 2, 3 and 5 are lower than their respective thresholds. The result of the test is determined by comparison with a pre-established matrix of outcomes: the result pattern High-Low-Low-High-Low is looked up in this table and found to generate a negative test result.

Figure 6:
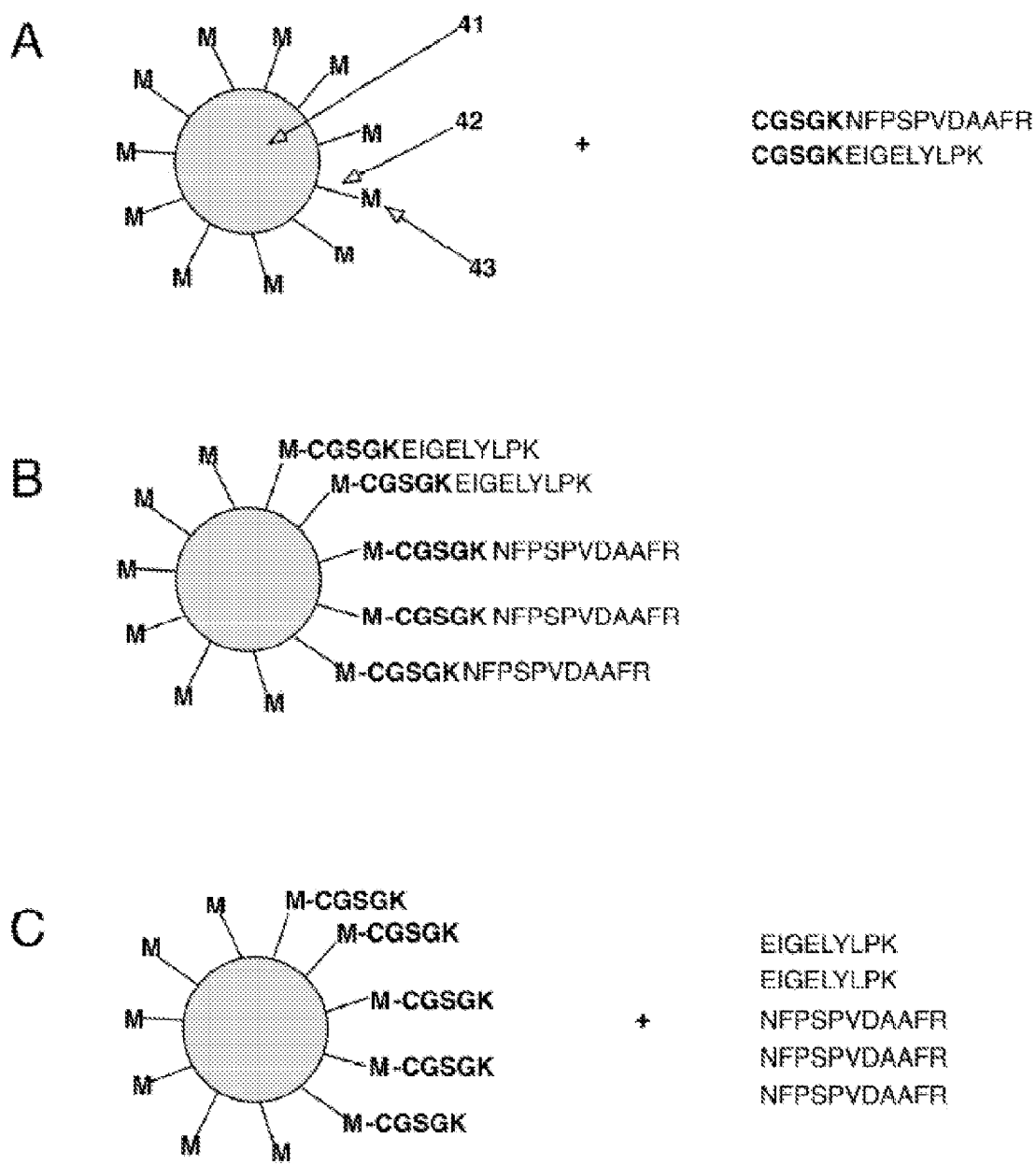
FIG. 6. Linkage to and release of extended SIS peptides from an activated carrier molecule. Extension sequence CGSGK SEQ ID No. 6, extended peptides CGSGKNFPSPVDAAFR and SEQ ID No. 8, CGSGKEIGELYPK SEQ ID No. 6, and released peptides NFPSPVDAAFR SEQ ID No. 7, and EIGELYLPK SEQ ID No. 5.

In a third example, a "carrierSIS protein" is prepared by linking extended SIS peptides to an activated protein carrier (as shown in FIGS. 6A and B). Carrier protein 1, in this case keyhole limpet hemocyanine (KLH), is activated by modification with multiple groups covalently attached to the KLH, each of which comprises a linker segment 2 and a maleimide reactive group 2 ("M"). This modification is accomplished by reaction of purified KLH with 4-(N-maleimidomethyl)cyclohexane-1-carboxylic acid 3-sulfo-N-hydroxysuccinimide ester (a heterobifunctional crosslinking reagent that reacts with protein primary amino groups to provide sulfhydryl-reactive maleimide groups on the protein surface).

SIS peptides are chemically synthesized with an n-terminal sequence extension containing a cysteine residue (whose sulfhydryl reacts with maleimide to yield a stable chemical bond), several spacer amino acids (here -GSG-, SEQ ID No. 1) and a final lysine (K) residue adjacent to the SIS n-terminus, creating a tryptic cleavage site. Peptide synthesis is typically carried out on a solid phase resin (Merrifield, Methods Enzymol 289:3-13, 1997), and can include steps to ligate together multiple synthetic peptides to produce larger peptides or proteins (Dawson, Muir, Clark-Lewis and Kent, Science 266:776-9, 1994, Dawson and Kent, Annu Rev Biochem 69:923-60, 2000). One embodiment makes use of stable isotope labeled K and R, since each tryptic SIS peptide contains only one such residue (either K or R) per peptide at the c-terminus, thus simplifying the calculation of mass shifts in the y-ion fragment series often used for selected reaction monitoring (SRM) quantitation in tandem mass spectrometry. Incorporation of labeled K or R is achieved through use of the corresponding labeled K or R synthons commercially available for solid phase peptide synthesis. Alternatively any amino acid containing stable isotope labels can be used.

Thus, the SIS peptide "EIGELYLPK*" (SEQ ID No. 5, corresponding to a tryptic peptide of human alpha-1-antichymotrypsin and incorporating a c-terminal stable isotope-labeled lysine shown as K* and described as $U^{-13}C_6$, 98%; $U^{-15}N_2$, 98%, thus, having a mass 8 amu greater than the unlabeled natural analyte peptide of the same sequence) is synthesized as the extended SIS peptide sequence "CGSGKEIGELYLPK*" (SEQ ID No. 6). This extended peptide reacts with activated KLH through reaction of the peptide's n-terminal cysteine sulfhydryl and a maleimide group on activated KLH. Action of trypsin on this extended SIS sequence bound to KLH cleaves between K and E residues, releasing the SIS sequence "EIGELYLPK*" (SEQ ID No. 5) without any extension and which is capable of functioning as a labeled internal standard for mass spectrometric measurement of EIGELYLPK (SEQ ID No. 5) (and thus indirectly of alpha-1-antichymotrypsin) in a sample digest. Similarly a second SIS peptide NFPSPVDAAFR* (SEQ ID No.7, a tryptic peptide of human hemopexin) is synthesized as the extended SIS "CGSGKNFPSPVDAAFR*" (SEQ ID No. 8) and reacted with activated KLH, combining with other maleimide groups on the activated KLH molecule. Action of trypsin on the bound extended SIS releases the SIS sequence NFPSPVDAAFR*, (SEQ ID No. 7) capable of functioning as a labeled internal standard for mass spectrometric measurement of sample-derived NFPSPVDAAFR (SEQ ID No. 7) and thus of the parent protein hemopexin.

To form the SIS peptide:carrier conjugate, a known amount of each SIS peptide (as established by quantitative amino acid analysis) is added to a 1.2 fold molar excess of activated KLH carrier (as determined by titration of available maleimide groups) and allowed to react for 6 hours (hr) at room temperature.

A known amount of carrierSIS (i.e., a known volume of standardized solution) is then added to a measured volume of a sample in which the target proteins are to be quantitated (in this case a sample of human blood plasma). This combined sample, including spiked carrierSIS standard, is then proteolytically digested by exposure to trypsin using any of a variety of well-known protocols. In one such protocol, plasma is denatured by addition of 9 volumes of 6 M guanidinium HCl/50 mM Tris-HCl/10 mM dithiothreitol and incubation for 2 hr at 60° C.; addition of 1 volume of 200 mM iodoacetamide followed by incubation for 30 min at 25 C; addition of 1 volume of 200 mM dithiothreitol followed by incubation for 30 min at 25 C; dilution to <1 M guanidinium HCl by addition of 50 mM NaHCO$_3$, addition of sequencing grade modified trypsin (e.g., from Promega, Madison, Wis.) at a 1:50 ratio (trypsin:plasma protein) and incubation overnight at 37° C. Digestion is allowed to proceed until substantially complete, liberating the monitor peptides from both target proteins and carrierSIS protein essentially to completion. Alternatively a mixture of SIS resulting from prior digestion of carrierSIS protein can be added to the sample before or after sample digestion. This sample digest now contains versions of analyte (monitor) peptides containing natural isotopes (from peptides derived from the original sample) and stable isotopes (in the SIS peptides derived from the carrier-SIS protein). Each sample-derived analyte monitor peptide can then be quantitated by measuring its concentration relative to the stable isotope version (which has a known concentration calculable from the amount spiked into the sample or sample digest) in a mass spectrometer, the results of which (an analyte:SIS ratio) then allows calculation of the concentration of the associated target protein in the initial sample (as described in published U.S. Pat. No. 7,632,686, High Sensitivity Quantitation Of Peptides By Mass Spectrometry, Anderson, Norman L.). In some embodiments, the relative concentrations of natural and stable isotope labeled monitor peptides can be measured by mass spectrometry as the relative ion currents recorded as peak intensity or area for the two peptides using electrospray-MS, or as peak intensity or area by MALDI-MS. The two versions of the peptide perform essentially identically in any chromatographic or affinity based separation or enrichment process (providing the elements N, C or O are used as stable isotope labels), and thus co-elute, facilitating direct comparison of ion currents. In this embodiment, one carrierSIS protein can replace an entire collection of separate SIS peptides described in earlier disclosures, and eliminates the requirement to separately store and handle the various SIS peptide reagents. Quantitative MS measurements can be made using a variety of ionization sources (e.g., electrospray ionization [ESI] and matrix-assisted laser desorption ionization [MALDI]) and mass analyzers (e.g., time-of-flight [TOF], triple quadrupole [TQMS], Fourier transform ion cyclotron resonance [FTICR], and ion trap).

The foregoing disclosure outlines a number of embodiments in terms of the SISCAPA method, and therefore represents one set of embodiments that may be employed in the application of the present technology. It will be appreciated that the methods and compositions disclosed herein are not limited to the SISCAPA method, but may be applied to other methods that employ internal peptide standards and the like.

The invention claimed is:

1. A carrier stable isotope standard (carrierSIS) complex comprising: a carrier having at least one carrier linkage site and at least one extended stable isotope standard (SIS) peptide having a peptide linkage site, wherein said SIS peptide is isotope labeled in one or more amino acids of said peptide;

wherein said carrier and said peptide are bound through a covalent linkage between said peptide linkage site and said carrier linkage site, wherein the linkage between said carrier linkage site and said peptide linkage site is not a proteolytic enzyme cleavage site, wherein said SIS peptide can be liberated from said carrier by action of a proteolytic process yielding at least one free SIS peptide that is chemically identical to the natural peptide for which said SIS peptide is a standard except for said isotope labeling, and wherein more than 90% of the SIS peptides bound to said carrier have the correct sequence compared to the natural peptide for which said SIS peptides are a standard.

2. The carrierSIS complex of claim 1, further comprising multiple different extended SIS peptides covalently bound to said carrier, wherein the multiple different extended SIS peptides are optionally bound to said carrier at different relative concentrations.

3. The carrierSIS complex of claim 1, wherein the carrier further comprises a moiety that can be assayed by spectrophotometry, fluorescence, mass spectrometry, an assay for the presence of biotin, or a moiety whose presence can measured by enzyme assay, thereby permitting an amount of carrier to be measured.

4. The carrierSIS complex of claim 1, wherein the carrier has one or more carrier quantitation peptides attached to it that can be released during proteolytic digestion, and which carrier quantitation peptides when released from said carrier permit quantitation of the carrier itself versus the SIS peptides bound to the carrier.

5. The carrierSIS complex of claim 1, wherein the carrier is a particle comprising non-protein components.

6. The carrierSIS complex of claim 2, wherein the multiple different extended SIS peptides are each separately bound to said carrier.

7. A carrier stable isotope standard (carrierSIS) complex comprising: a carrier having at least one carrier linkage site and at least one extended stable isotope standard (SIS) peptide having a peptide linkage site;
  wherein said carrier and said peptide are bound through a covalent linkage between said peptide linkage site and said carrier linkage site, wherein the linkage between said carrier linkage site and said peptide linkage site is not a proteolytic enzyme cleavage site,
  wherein said SIS peptide can be liberated from said carrier by action of a proteolytic process yielding at least one free SIS peptide,
  wherein more than 90% of the SIS peptides bound to said carrier have the correct sequence compared to the natural peptide for which said SIS peptides are a standard,
  and wherein the carrier is a magnetic particle.

8. The carrierSIS complex of claim 7, wherein the magnetic particle is a magnetic bead.

9. The carrierSIS complex of claim 8, wherein the magnetic bead has a diameter of from about 1,000 nanometers to about 100,000 nanometers.

10. The carrierSIS complex of claim 1, wherein the carrier is a molecule.

11. The carrierSIS complex of claim 10, wherein said molecule is a protein molecule or polymer containing linkage sites.

12. The carrierSIS complex of claim 1, wherein the carrier is a particle selected from the group consisting of: a magnetic particle, a polymer particle, a POROS bead, a polystyrene particle, a controlled-pore glass particle, and an agarose bead.

13. A carrier stable isotope standard (carrierSIS) complex comprising: a carrier having at least one carrier linkage site and at least one extended stable isotope standard (SIS) peptide having a peptide linkage site;
  wherein said carrier and said peptide are bound through a covalent linkage between said peptide linkage site and said carrier linkage site, wherein the linkage between said carrier linkage site and said peptide linkage site is not a proteolytic enzyme cleavage site,
  wherein said SIS peptide can be liberated from said carrier by action of a proteolytic process yielding at least one free SIS peptide,
  wherein more than 90% of the SIS peptides bound to said carrier have the correct sequence compared to the natural peptide for which said SIS peptides are a standard,
  and wherein the at least one extended SIS peptide is an extended polySIS peptide comprising different SISpeptide sequences in different relative proportions.

14. An assay kit, comprising:
  (a) a carrierSIS complex comprising: a carrier having at least one carrier linkage site and at least one extended SIS peptide having a peptide linkage site;
  wherein said carrier and said peptide are bound through a covalent linkage between said peptide linkage site and said carrier linkage site, wherein the linkage between said carrier linkage site and said peptide linkage site is not a proteolytic enzyme cleavage site,
  wherein said SIS peptide can be liberated from said carrier by action of a proteolytic process yielding at least one free SIS peptide, and
  (b) antibodies specific to said at least one free SIS peptide.

15. The kit of claim 14, wherein the carrier is a particle containing non-protein components.

16. The kit of claim 15, wherein the multiple different extended SIS peptides are each separately bound to said carrier.

17. The kit of claim 14, wherein the carrier is a magnetic particle.

18. The kit of claim 17, wherein the magnetic particle is a magnetic bead.

19. The kit of claim 18, wherein the magnetic bead has a diameter of from about 1,000 nanometers to about 100,000 nanometers.

20. The kit of claim 14, wherein more than 90% of the SIS peptides bound to said carrier have the correct sequence compared to the natural peptide for which the SIS peptides are a standard.

21. The carrierSIS complex of claim 1, wherein said carrier is a polymeric molecule comprising a polysaccharide.

22. The carrierSIS complex of claim 14, wherein said carrier is a polymeric molecule comprising a polysaccharide.

23. The carrierSIS complex of claim 1, wherein each said SIS peptide contains at least one site at which a non-predominant stable isotope label is substituted for the predominant naturally occurring isotope of the atom appearing at that site in more than 95% of the SIS peptides bound to said carrier.

24. The carrierSIS complex of claim 14, wherein each said SIS peptide contains at least one site at which a non-predominant stable isotope label is substituted for the predominant naturally occurring isotope of the atom appearing at that site in more than 95% of the SIS peptides bound to said carrier.

* * * * *